(12) United States Patent
Worrell

(10) Patent No.: US 11,819,260 B2
(45) Date of Patent: *Nov. 21, 2023

(54) DETENT FEATURE FOR ARTICULATION CONTROL IN SURGICAL INSTRUMENT

(71) Applicant: Cilag GmbH International, Zug (CH)

(72) Inventor: Barry C. Worrell, Centerville, OH (US)

(73) Assignee: Cilag GmbH International, Zug (CH)

( * ) Notice: Subject to any disclaimer, the term of this patent is extended or adjusted under 35 U.S.C. 154(b) by 71 days.

This patent is subject to a terminal disclaimer.

(21) Appl. No.: 17/159,547

(22) Filed: Jan. 27, 2021

(65) Prior Publication Data
US 2021/0212752 A1    Jul. 15, 2021

Related U.S. Application Data

(63) Continuation of application No. 15/499,359, filed on Apr. 27, 2017, now Pat. No. 10,932,845.

(51) Int. Cl.
*A61B 17/00* (2006.01)
*A61B 18/14* (2006.01)
(Continued)

(52) U.S. Cl.
CPC ...... *A61B 18/1445* (2013.01); *A61B 17/2841* (2013.01); *A61B 17/29* (2013.01);
(Continued)

(58) Field of Classification Search
CPC . A16B 18/1445; A16B 18/12; A61B 17/2841; A61B 17/29; A61B 17/2909;
(Continued)

(56) References Cited

U.S. PATENT DOCUMENTS

| | | |
|---|---|---|
| 4,805,823 A | 2/1989 | Rothfuss |
| 5,415,334 A | 5/1995 | Williamson et al. |

(Continued)

FOREIGN PATENT DOCUMENTS

| | | |
|---|---|---|
| CN | 104640509 A | 5/2021 |
| EP | 2889005 A1 | 7/2015 |

(Continued)

OTHER PUBLICATIONS

European Search Report, Supplementary, and Written Opinion dated Dec. 4, 2020, for Application No. 18791839.6, 11 pages.

(Continued)

*Primary Examiner* — Joanne M Rodden
*Assistant Examiner* — Rachel A. Vierra
(74) *Attorney, Agent, or Firm* — Frost Brown Todd LLP

(57) ABSTRACT

An apparatus includes a body, a shaft assembly, an articulation section, an end effector, and an articulation drive assembly. The articulation drive assembly is configured to drive the articulation section to deflect the end effector relative to the longitudinal axis from a non-articulated configuration to an articulated configuration. The articulation drive assembly includes a rotatable housing, a static member, and an indication feature. The rotatable housing is rotatably coupled to the body. The static member is fixed relative to the body. The indication feature is configured to indicate when the end effector is deflected into the non-articulated configuration. The indication feature includes a ridge and a cantilever arm. The ridge extends from an exterior surface of the rotatable housing. The cantilever arm defines a slot configured to house the ridge when the end effector is in the non-articulated configuration.

20 Claims, 27 Drawing Sheets

(51) Int. Cl.

| | | |
|---|---|---|
| A61B 18/00 | (2006.01) | |
| A61B 17/29 | (2006.01) | |
| A61B 90/00 | (2016.01) | |
| A61B 17/28 | (2006.01) | |
| A61B 18/12 | (2006.01) | |

(52) U.S. Cl.
CPC ........... *A61B 17/2909* (2013.01); *A61B 18/12* (2013.01); *A61B 2017/00305* (2013.01); *A61B 2017/00309* (2013.01); *A61B 2017/00327* (2013.01); *A61B 2018/00202* (2013.01); *A61B 2090/0811* (2016.02)

(58) Field of Classification Search
CPC ........... A61B 2018/00202; A61B 2017/00305; A61B 2017/00309; A61B 2017/00327
See application file for complete search history.

(56) References Cited

U.S. PATENT DOCUMENTS

| | | | |
|---|---|---|---|
| 5,465,895 A | 11/1995 | Knodel et al. | |
| 5,597,107 A | 1/1997 | Knodel et al. | |
| 5,632,432 A | 5/1997 | Schulze et al. | |
| 5,673,840 A | 10/1997 | Schulze et al. | |
| 5,704,534 A | 1/1998 | Huitema et al. | |
| 5,814,055 A | 9/1998 | Knodel et al. | |
| 6,500,176 B1 | 12/2002 | Truckai et al. | |
| 6,783,524 B2 | 8/2004 | Anderson et al. | |
| 6,978,921 B2 | 12/2005 | Shelton et al. | |
| 7,000,818 B2 | 2/2006 | Shelton et al. | |
| 7,112,201 B2 | 9/2006 | Truckai et al. | |
| 7,125,409 B2 | 10/2006 | Truckai et al. | |
| 7,143,923 B2 | 12/2006 | Shelton et al. | |
| 7,169,146 B2 | 1/2007 | Truckai et al. | |
| 7,186,253 B2 | 3/2007 | Truckai et al. | |
| 7,189,233 B2 | 3/2007 | Truckai et al. | |
| 7,220,951 B2 | 5/2007 | Truckai et al. | |
| 7,303,108 B2 | 12/2007 | Shelton et al. | |
| 7,309,849 B2 | 12/2007 | Truckai et al. | |
| 7,311,709 B2 | 12/2007 | Truckai et al. | |
| 7,354,440 B2 | 4/2008 | Truckai et al. | |
| 7,367,485 B2 | 5/2008 | Shelton et al. | |
| 7,380,695 B2 | 6/2008 | Doll et al. | |
| 7,380,696 B2 | 6/2008 | Shelton et al. | |
| 7,381,209 B2 | 6/2008 | Truckai et al. | |
| 7,404,508 B2 | 7/2008 | Smith et al. | |
| 7,434,715 B2 | 10/2008 | Shelton et al. | |
| 7,721,930 B2 | 5/2010 | McKenna et al. | |
| 8,408,439 B2 | 4/2013 | Huang et al. | |
| 8,453,914 B2 | 6/2013 | Laurent et al. | |
| 8,461,744 B2 | 6/2013 | Wiener et al. | |
| 8,888,809 B2 | 11/2014 | Davison et al. | |
| 8,939,974 B2 | 1/2015 | Boudreaux et al. | |
| 8,986,302 B2 | 3/2015 | Aldridge et al. | |
| 9,089,327 B2 | 7/2015 | Worrell et al. | |
| 9,161,803 B2 | 10/2015 | Yates et al. | |
| 9,402,682 B2 | 8/2016 | Worrell et al. | |
| 9,492,224 B2 | 11/2016 | Boudreaux et al. | |
| 9,526,565 B2 | 12/2016 | Strobel | |
| 9,545,253 B2 | 1/2017 | Worrell et al. | |
| 10,010,340 B2 | 7/2018 | Hibner et al. | |
| 10,932,845 B2 | 3/2021 | Worrell | |
| 2005/0006430 A1 | 1/2005 | Wales | |
| 2006/0079874 A1 | 4/2006 | Faller et al. | |
| 2007/0191713 A1 | 8/2007 | Eichmann et al. | |
| 2007/0282333 A1 | 12/2007 | Fortson et al. | |
| 2008/0200940 A1 | 8/2008 | Eichmann et al. | |
| 2011/0288452 A1 | 11/2011 | Houser et al. | |
| 2012/0078243 A1 | 3/2012 | Worrell et al. | |
| 2013/0023868 A1* | 1/2013 | Worrell ............ | A61B 17/07207 606/205 |
| 2014/0371737 A1 | 12/2014 | Korvick et al. | |
| 2016/0100882 A1 | 4/2016 | Boudreaux et al. | |
| 2016/0296268 A1 | 10/2016 | Gee et al. | |
| 2016/0302820 A1 | 10/2016 | Hibner et al. | |

FOREIGN PATENT DOCUMENTS

| | | |
|---|---|---|
| EP | 2997923 A1 | 3/2016 |
| WO | WO 2016/168558 A2 | 10/2016 |

OTHER PUBLICATIONS

International Search Report and Written Opinion dated Jul. 5, 2018, for International Application No. PCT/US2018/027781, 9 pages.
U.S. Appl. No. 61/410,603, entitled "Energy-Based Surgical Instruments," filed Nov. 5, 2010.
Chinese Office Action, The First Office Action, and First Search Report, dated Sep. 6, 2022 for Application No. CN 201880031804.4, 10 pgs.
Japanese Office Action, Notification of Reasons for Refusal, and Search Report by Registered Search Organization, dated Mar. 15, 2022 for Application No. JP 2019-558611, 28 pgs.

* cited by examiner

DETENT FEATURE FOR ARTICULATION CONTROL IN SURGICAL INSTRUMENT

This application is a continuation of U.S. patent application Ser. No. 15/499,359, entitled "Detent Feature for Articulation Control in Surgical Instrument," filed Apr. 27, 2017, published as U.S. Pub. No. 2018/0310982 on Nov. 1, 2018, issued as U.S. Pat. No. 10,932,845 on Mar. 2, 2021.

BACKGROUND

A variety of surgical instruments include a tissue cutting element and one or more elements that transmit radio frequency (RF) energy to tissue (e.g., to coagulate or seal the tissue). An example of such an electrosurgical instrument is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Additional examples of electrosurgical cutting instruments and related concepts are disclosed in U.S. Pub. No. 2011/0087218, entitled "Surgical Instrument Comprising First and Second Drive Systems Actuatable by a Common Trigger Mechanism," published Apr. 14, 2011, issued as U.S. Pat. No. 8,939,974 on Jan. 27, 2015, the disclosure of which is incorporated by reference herein; U.S. Pub. No. 2012/0083783, entitled "Surgical Instrument with Jaw Member," published Apr. 5, 2012, issued as U.S. Pat. No. 8,888,809 on Nov. 18, 2014, the disclosure of which is incorporated by reference herein; U.S. Pub. No. 2012/0116379, entitled "Motor Driven Electrosurgical Device with Mechanical and Electrical Feedback," published May 10, 2012, issued as U.S. Pat. No. 9,161,803 on Oct. 20, 2015, the disclosure of which is incorporated by reference herein; U.S. Pub. No. 2012/0078243, entitled "Control Features for Articulating Surgical Device," published Mar. 29, 2012, issued as U.S. Pat. No. 9,877,720 on Jan. 30, 2018, the disclosure of which is incorporated by reference herein; U.S. Pub. No. 2012/0078247, entitled "Articulation Joint Features for Articulating Surgical Device," published Mar. 29, 2012, issued as U.S. Pat. No. 9,402,682 on Aug. 2, 2016 the disclosure of which is incorporated by reference herein; U.S. Pub. No. 2013/0030428, entitled "Surgical Instrument with Multi-Phase Trigger Bias," published Jan. 31, 2013, issued as U.S. Pat. No. 9,089,327 on Jul. 28, 2015, the disclosure of which is incorporated by reference herein; and U.S. Pub. No. 2013/0023868, entitled "Surgical Instrument with Contained Dual Helix Actuator Assembly," published Jan. 31, 2013, issued as U.S. Pat. No. 9,545,253 on Jan. 17, 2017, the disclosure of which is incorporated by reference herein.

Still other examples of electrosurgical cutting instruments and related concepts are disclosed in U.S. Pat. No. 9,526,565, entitled "Electrosurgical Devices," issued Dec. 27, 2016, the disclosure of which is incorporated by reference herein; U.S. Pat. No. 9,492,224, entitled "Multi-Function Bi-Polar Forceps," issued Nov. 15, 2016, the disclosure of which is incorporated by reference herein; and U.S. Pub. No. 2016/0100882, entitled "Methods and Devices for Articulating Laparoscopic Energy Device," published Apr. 14, 2016, issued as U.S. Pat. No. 10,292,758 on May 21, 2019, the disclosure of which is incorporated by reference herein.

While a variety of surgical instruments have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
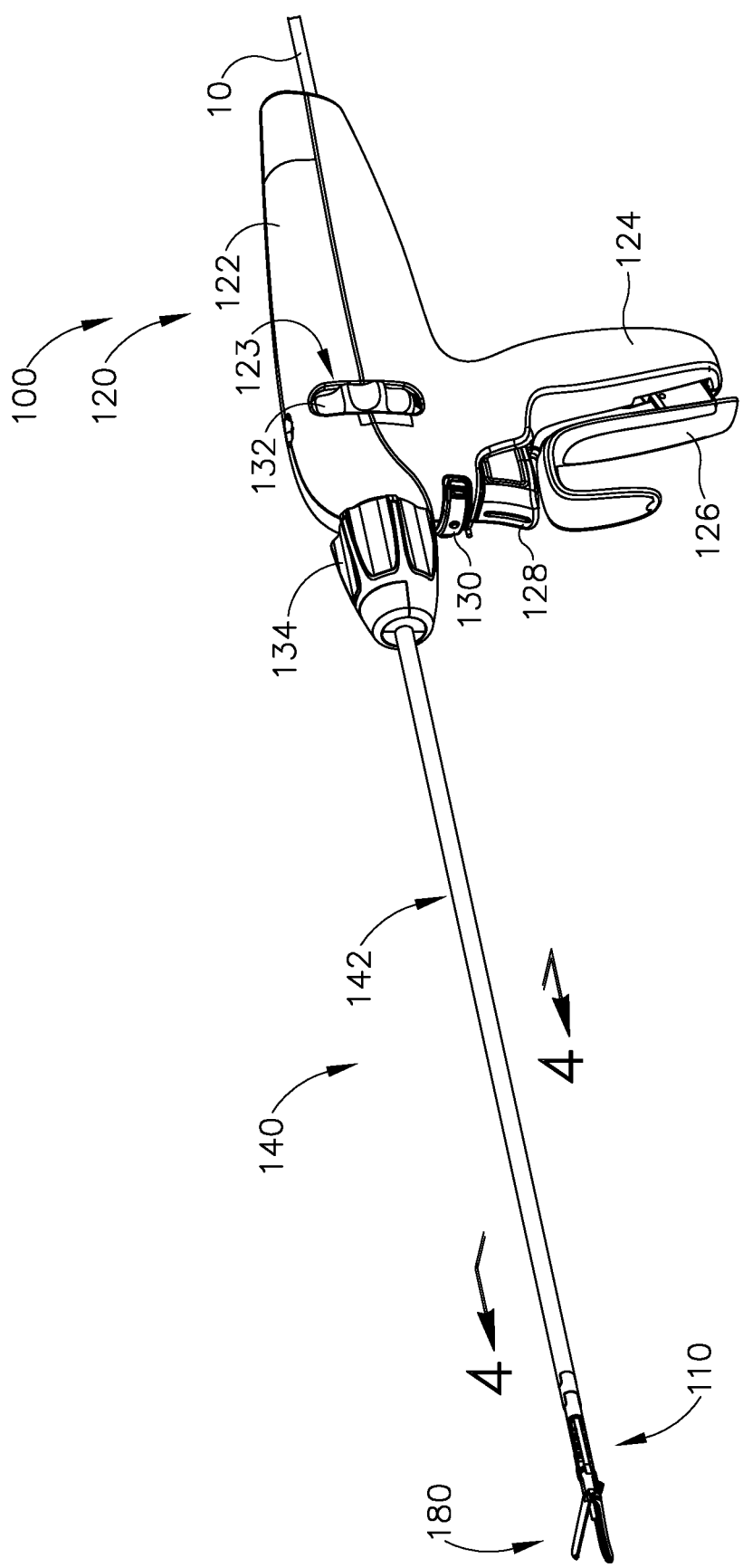
FIG. 1 depicts a perspective view of an exemplary electrosurgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a surgeon or other operator grasping a surgical instrument having a distal surgical end effector. The term "proximal" refers the position of an element closer to the surgeon or other operator and the term "distal" refers to the position of an element closer to the surgical end effector of the surgical instrument and further away from the surgeon or other operator.

I. Exemplary Electrosurgical Instrument

FIGS. 1-10 show an exemplary electrosurgical instrument (100). As best seen in FIG. 1, electrosurgical instrument (100) includes a handle assembly (120), a shaft assembly (140), an articulation assembly (110), and an end effector (180). As will be described in greater detail below, end effector (180) of electrosurgical instrument (100) is operable to grasp, cut, and seal or weld tissue (e.g., a blood vessel, etc.). In this example, end effector (180) is configured to seal or weld tissue by applying bipolar radio frequency (RF) energy to tissue. However, it should be understood electrosurgical instrument (100) may be configured to seal or weld tissue through any other suitable means that would be apparent to one having ordinary skill in the art in view of the teachings herein. For example, electrosurgical instrument (100) may be configured to seal or weld tissue via an ultrasonic blade, staples, etc. In the present example, electrosurgical instrument (100) is electrically coupled to a power source (not shown) via power cable (10).

The power source may be configured to provide all or some of the electrical power requirements for use of electrosurgical instrument (100). Any suitable power source may be used as would be apparent to one having ordinary skill in the art in view of the teachings herein. By way of example only, the power source may comprise a GEN04 or GEN11 sold by Ethicon Endo-Surgery, Inc. of Cincinnati, Ohio. In addition, or in the alternative, the power source may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. While in the current example, electrosurgical instrument (100) is coupled to a power spruce via power cable (10), electrosurgical instrument (100) may contain an internal power source or plurality of power sources, such as a battery and/or supercapacitors, to electrically power electrosurgical instrument (100). Of course, any suitable combination of power sources may be utilized to power electrosurgical instrument (100) as would be apparent to one having ordinary skill in the art in view of the teaching herein.

Handle assembly (120) is configured to be grasped by an operator with one hand, such that an operator may control and manipulate electrosurgical instrument (100) with a single hand. Shaft assembly (140) extends distally from handle assembly (120) and connects to articulation assembly (110). Articulation assembly (110) is also connected to a proximal end of end effector (180). As will be described in greater detail below, components of handle assembly (120) are configured to control end effector (180) such that an operator may grasp, cut, and seal or weld tissue. As will also be described in greater detail below, articulation assembly (110) is configured to deflect end effector (180) from the longitudinal axis defined by shaft assembly (140).

Handle assembly (120) includes a body (122), a pistol grip (124), a jaw closure trigger (126), a knife trigger (128), an activation button (130), an articulation control (132), and a knob (134). As will be described in greater detail below, jaw closure trigger (126) may be pivoted toward and away from pistol grip (124) and/or body (122) to open and close jaws (182, 184) of end effector (180) to grasp tissue. Knife trigger (128) may be pivoted toward and away from pistol grip (124) and/or body (122) to actuate a knife member (360) within the confines of jaws (182, 184) to cut tissue captured between jaws (182, 184). Activation button (130) may be pressed to apply radio frequency (RF) energy to tissue via electrode surfaces (194, 196) of jaws (182, 184), respectively.

Body (122) of handle assembly (120) defines an opening (123) in which a portion of articulation control (132) protrudes from. Articulation control (132) is rotatably disposed within body (122) such that an operator may rotate the portion of articulation control (132) protruding from opening (123) to rotate the portion of articulation control (132) located within body (122). As will be described in greater detail below, rotation of articulation control (132) relative to body (122) will drive deflection of end effector (180) from the longitudinal axis defined by shaft assembly (140).

Knob (134) is rotatably disposed on the distal end of body (122) and configured to rotate end effector (180), articulation assembly (110), and shaft assembly (140) about the longitudinal axis of shaft assembly (140) relative to handle assembly (120). While in the current example, end effector (180), articulation assembly (110), and shaft assembly (140) are rotated by knob (134), knob (134) may be configured to rotate end effector (180) and articulation assembly (110) relative to selected portions of shaft assembly (140). Knob (134) may include any suitable features to rotate end effector (180), articulation assembly (110), and shaft assembly (140) as would be apparent to one having ordinary skill in the art in view of the teachings herein.

Figure 4:
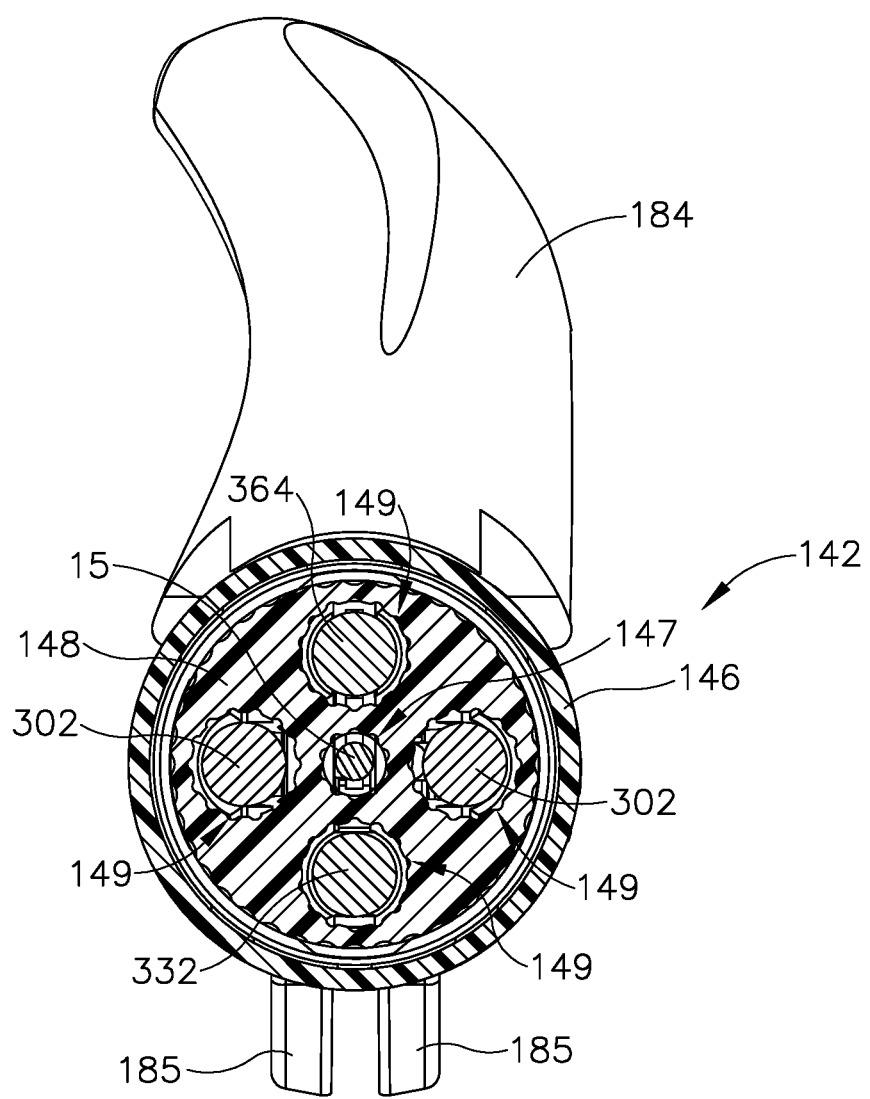
FIG. 4 depicts a cross-sectional rear view of a shaft assembly of the electrosurgical instrument of FIG. 1, taken along line 4-4 of FIG. 1.
Figure 7A:
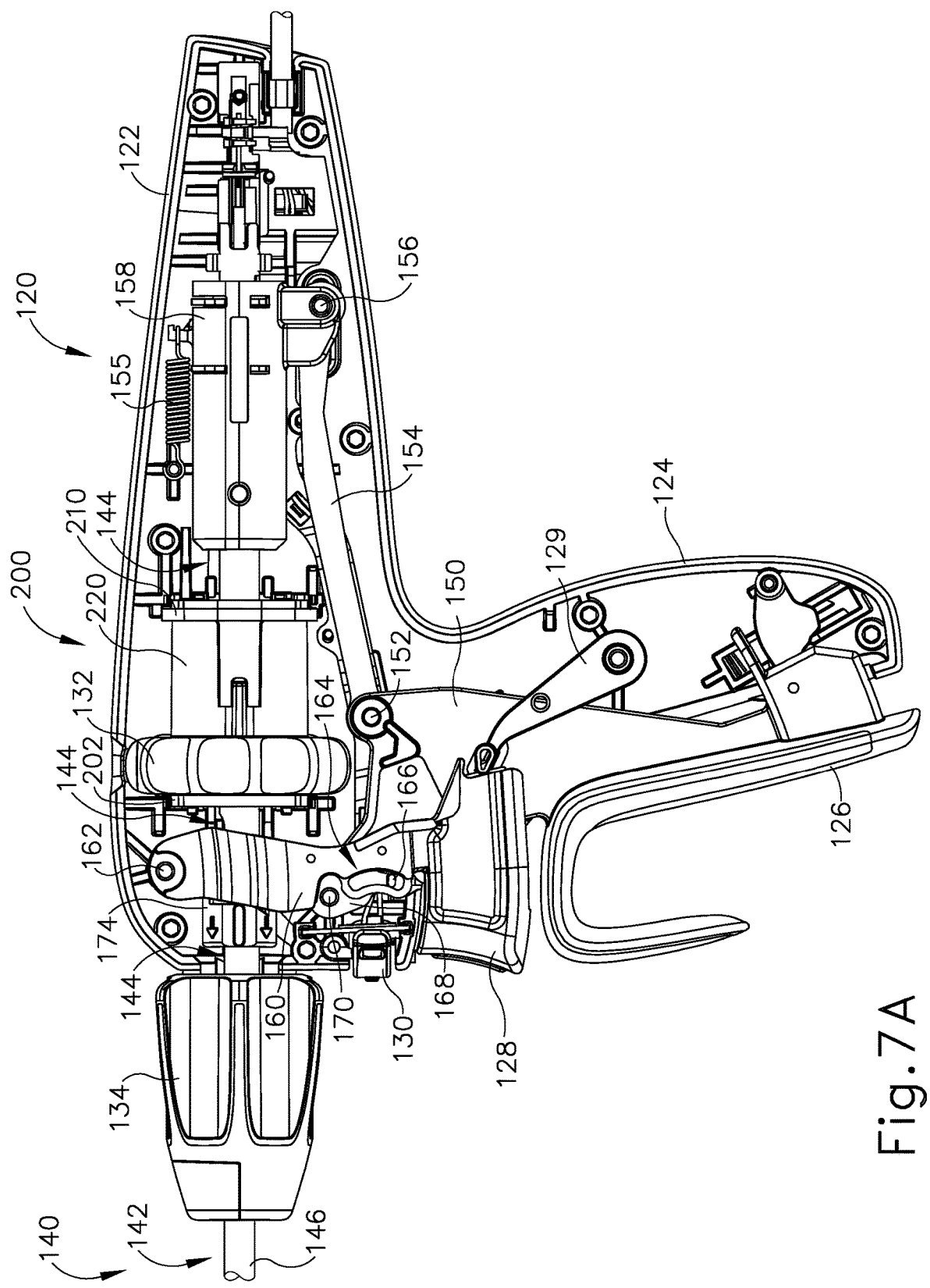
FIG. 7A depicts a side elevational view of a handle assembly of the electrosurgical instrument of FIG. 1, where the end effector is in an open and unfired state, where a portion of the handle assembly is omitted for purposes of clarity.
Figure 7B:
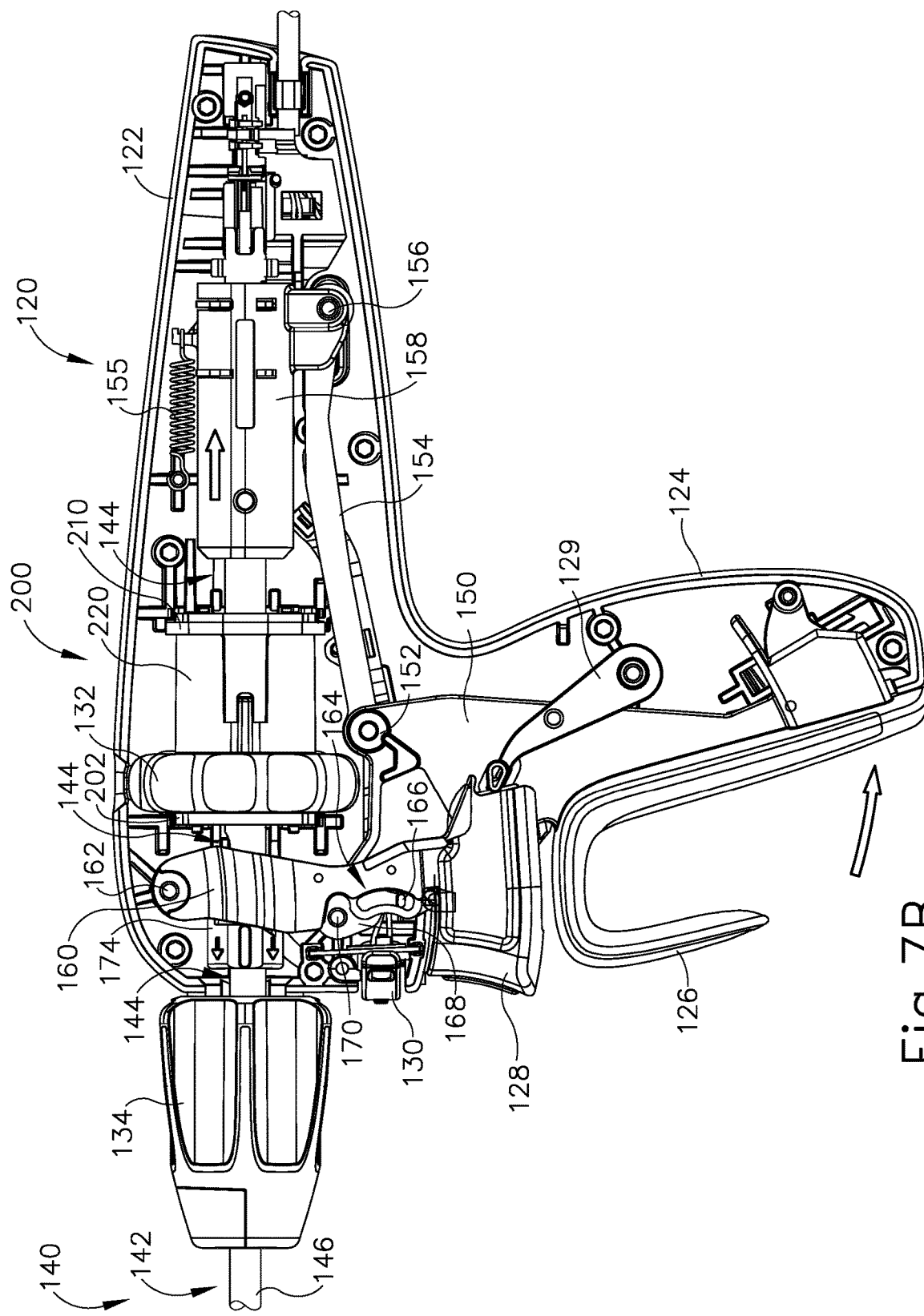
FIG. 7B depicts a side elevational view of the handle assembly of FIG. 7A, where the end effector is in a closed and unfired state, where a portion of the handle assembly is omitted for purposes of clarity.
Figure 7C:
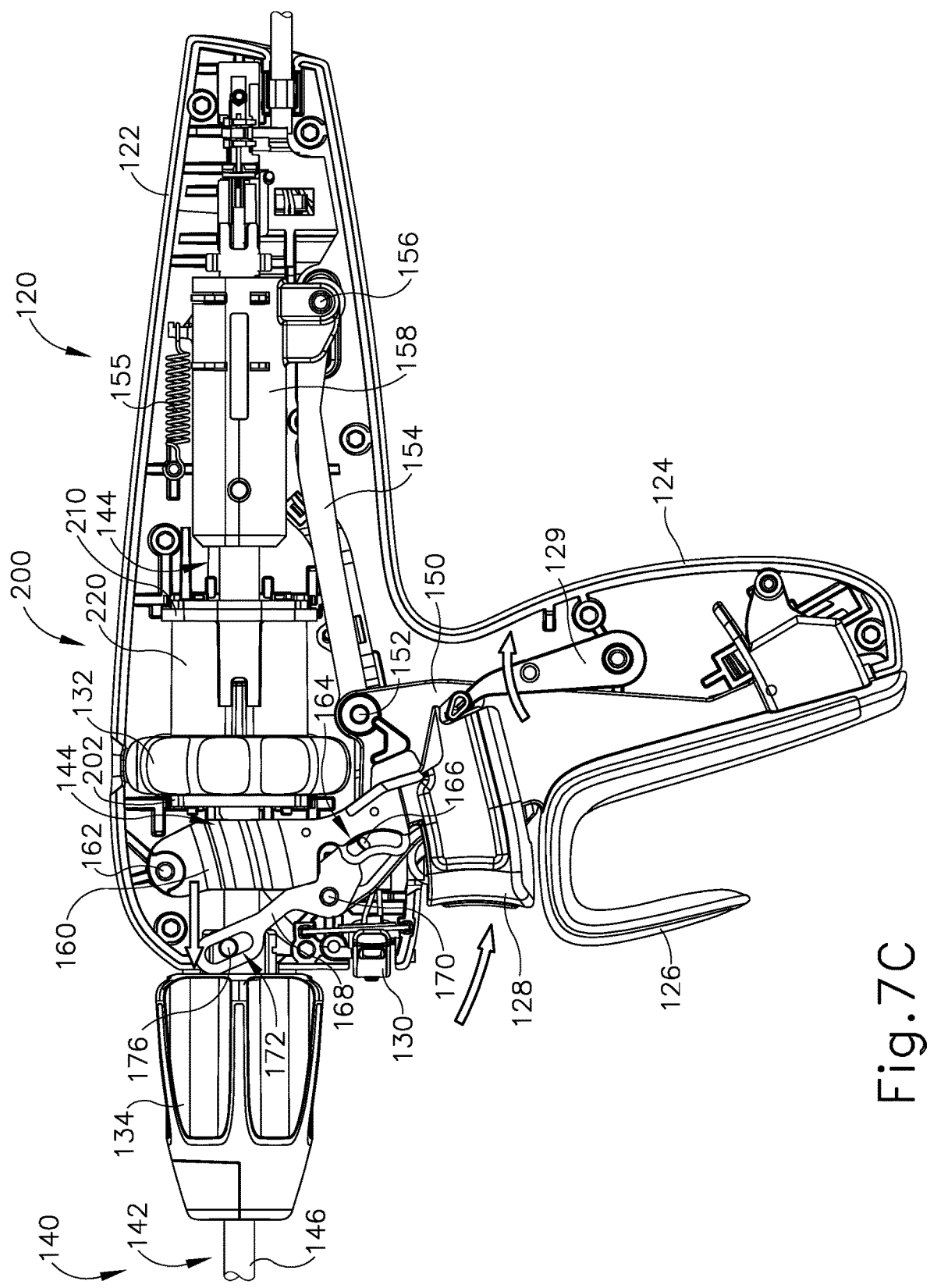
FIG. 7C depicts a side elevational view of the handle assembly of FIG. 7A, where the end effector is in a closed and fired state, where a portion of the handle assembly is omitted for purposes of clarity.

As best seen in FIGS. 7A-7C, shaft assembly (140) includes distal portion (142) extending distally from handle assembly (120), and a proximal portion (144) housed within the confines of body (122) of handle assembly (120). As seen in FIG. 4, distal portion (142) of shaft assembly (140) includes an external sheath (146) and a housing member (148) disposed within external sheath (146). Housing member (148) defines four longitudinal pathways (149) disposed around a central longitudinal pathway (147). Longitudinal pathways (149) slidably house two rod portions (302) of two articulation connectors (300), a rod portion (332) of jaw closure connector (330), and a knife rod (364) of knife member (360); while central longitudinal pathway (147) houses electrical coupling (15). As will be described in greater detail below, articulation connectors (300) are configured to couple certain actuating portions of handle assembly (120) with end effector (180). Articulation connectors (300) are configured to translate relative to shaft assembly (140) to drive articulation of end effector (180) relative to the longitudinal axis defined by shaft assembly (140). As will also be described in greater detail below, jaw closure connector (330) is configured to couple an actuating portion of handle assembly (120) with end effector (180). Jaw closure connector (330) is configured to translate relative to shaft assembly (140) to open and close jaws (182, 184) of end effector (180). As will also be described in greater detail below, knife member (360) is configured to couple to an actuating portion of handle assembly (120) to translate a distal cutting edge (362) within the confines of end effector (180).

Figure 9A:
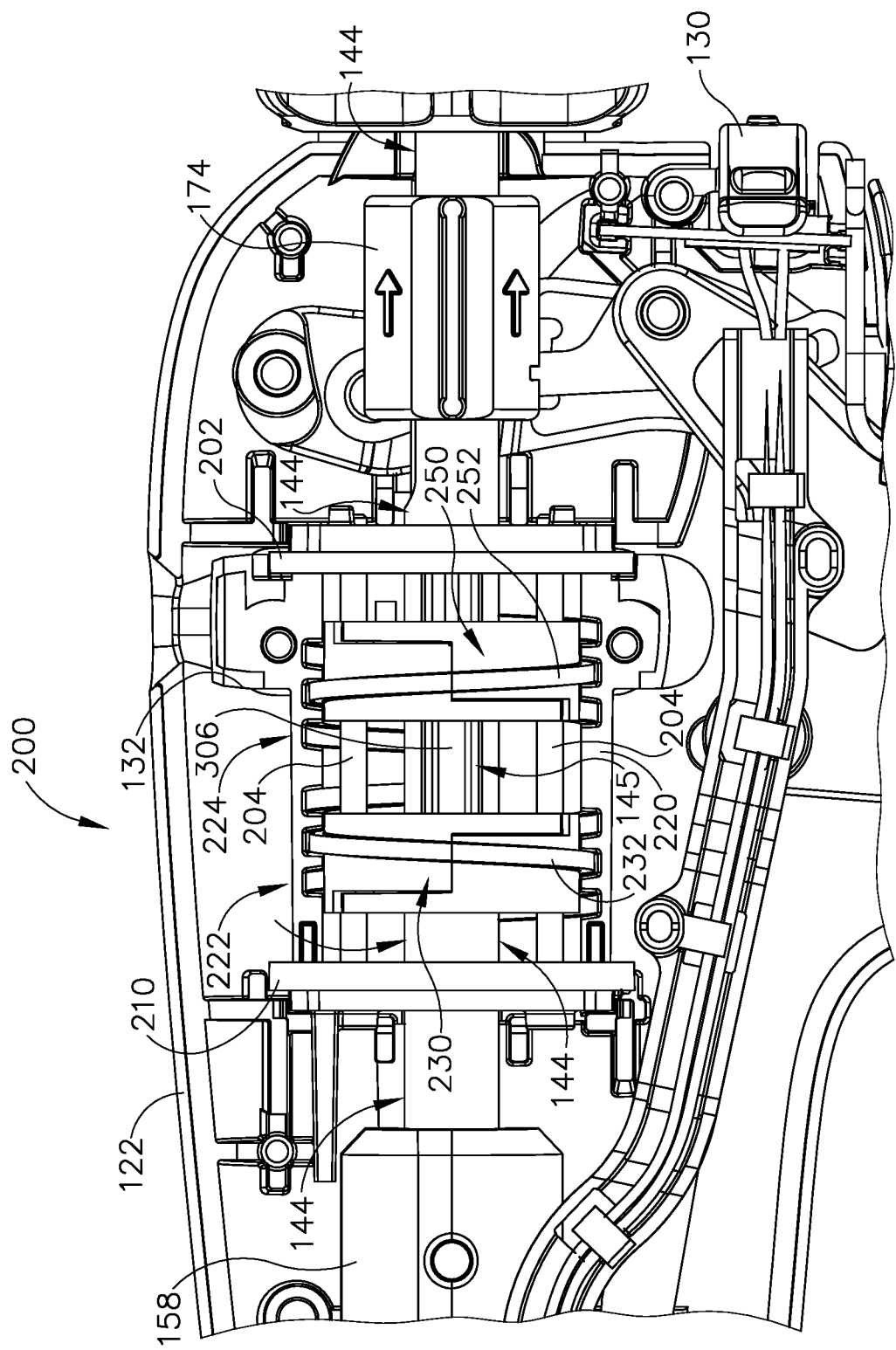
FIG. 9A depicts an elevational side view of the handle assembly of FIG. 7A, where the articulation assembly of FIG. 2 is a non-articulated configuration, where selected portions of the handle assembly are omitted for purposes of clarity.
Figure 9B:
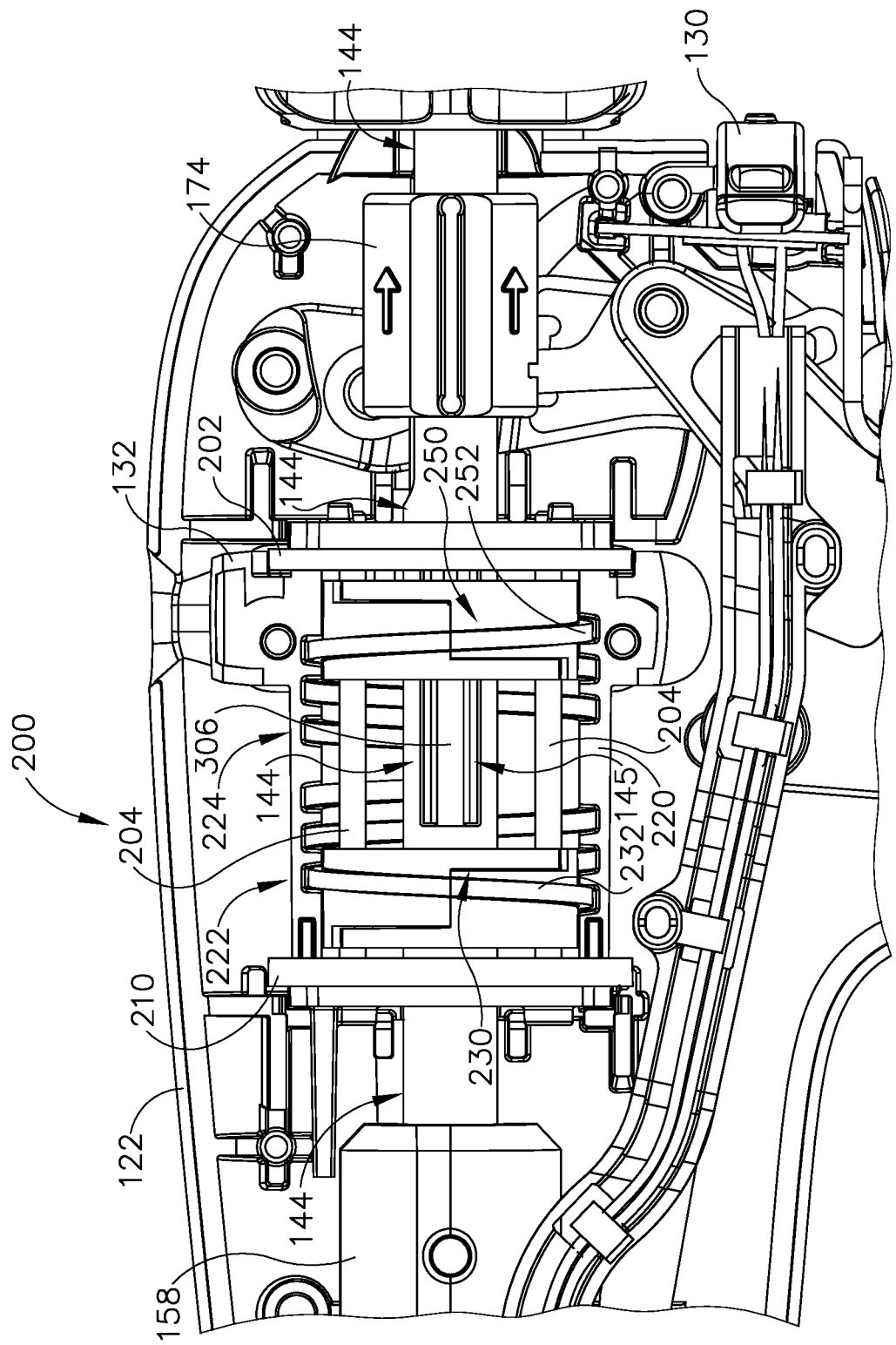
FIG. 9B depicts an elevational side view of the handle assembly of FIG. 7A, where the articulation assembly of FIG. 2 is in a first articulated configuration, were selected portions of the handle assembly are omitted for purposes of clarity.
Figure 9C:
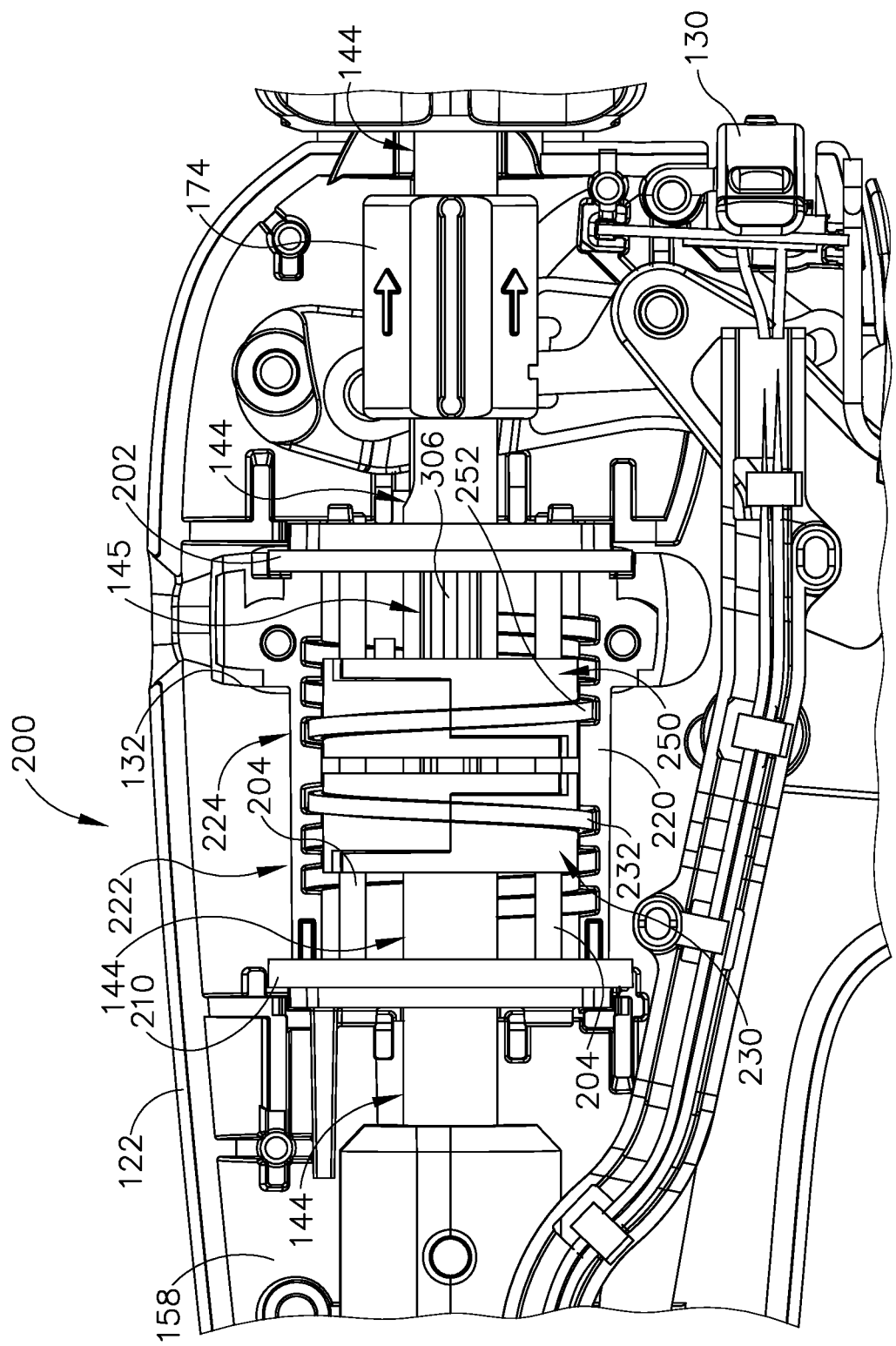
FIG. 9C depicts an elevational side view of the handle assembly of FIG. 7A, where the articulation assembly of FIG. 2 is in a second articulated configuration, were selected portions of the handle assembly are omitted for purposes of clarity.

As will be described in greater detail below, proximal portion (144) of shaft assembly (140) extends within handle assembly (120) and through certain actuating portions of handle assembly (120) that are configured to longitudinally drive rod portions (302, 332, 364). As will also be described in greater detail below, rod portions (302, 332, 364) extend within proximal portion (144) and couple with correspond actuating portions of handle assembly (120). As best shown in FIGS. 9A-9C, proximal portion (144) defines slots (145) to allow actuating portions of handle assembly (120) to couple with rod portions (302, 332, 364) such that translation of actuation portions of handle assembly (120) relative to shaft assembly (140) longitudinally drives rod portions (302, 332, 364) relative to shaft assembly (140). Rod portions (302, 332, 364) are coupled to certain actuating portions of handle assembly (120) such that rod portions (302, 332, 364) may rotate with shaft assembly (140) relative to actuating portions of handle assembly (120); but also such that rod portions (302, 332, 364) longitudinally translate with actuating portions of handle assembly (120) relative to shaft assembly (140). In other words, an operator may utilize knob (134) to rotate shaft assembly (140) and rod portions (302, 332, 364) relative to handle assembly (120); but also may actuate rod portions (302, 332, 364) longitudinally relative to shaft assembly (140).

Figure 2:
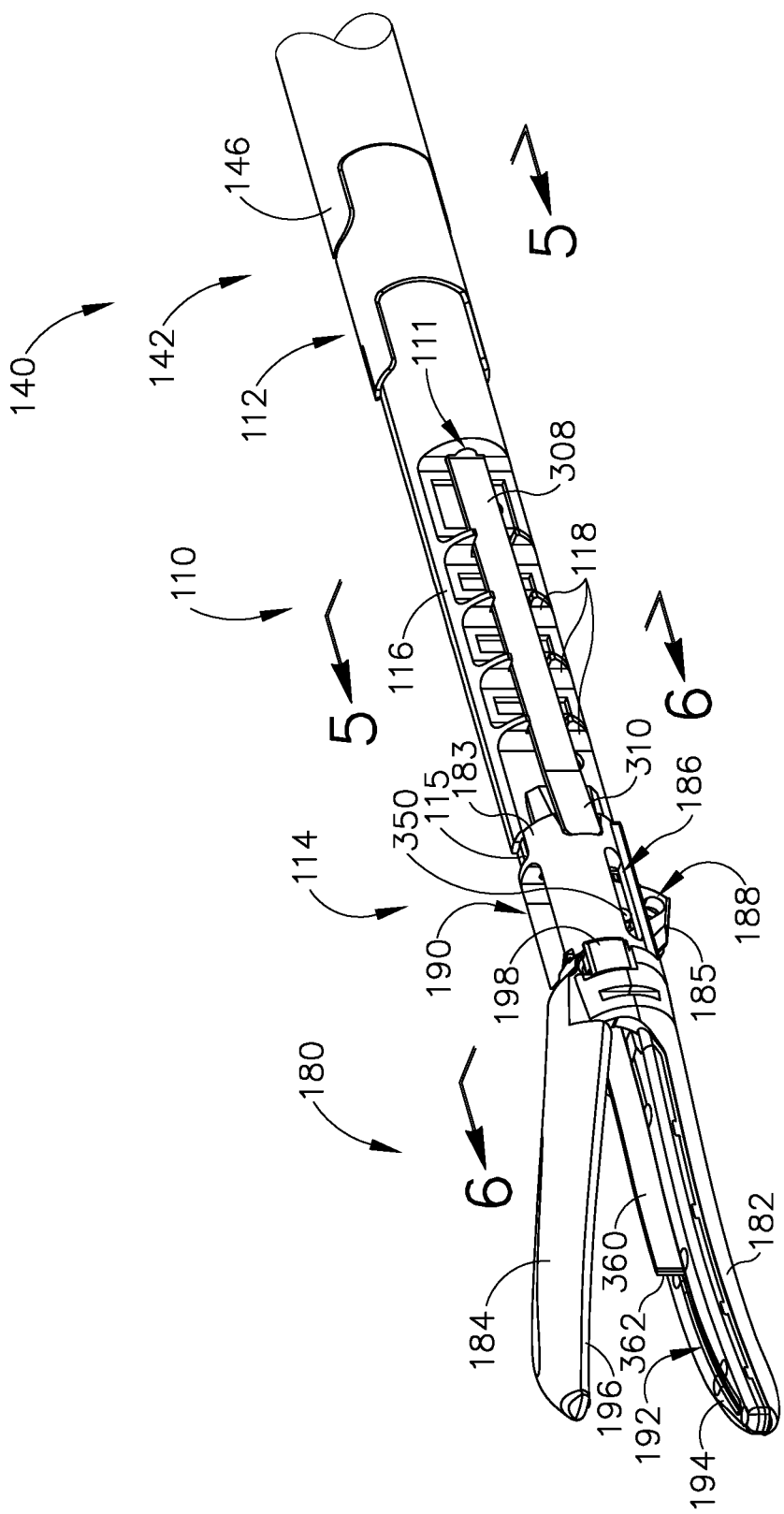
FIG. 2 depicts a perspective view of an exemplary articulation assembly and end effector of the electrosurgical instrument of FIG. 1.
Figure 3:
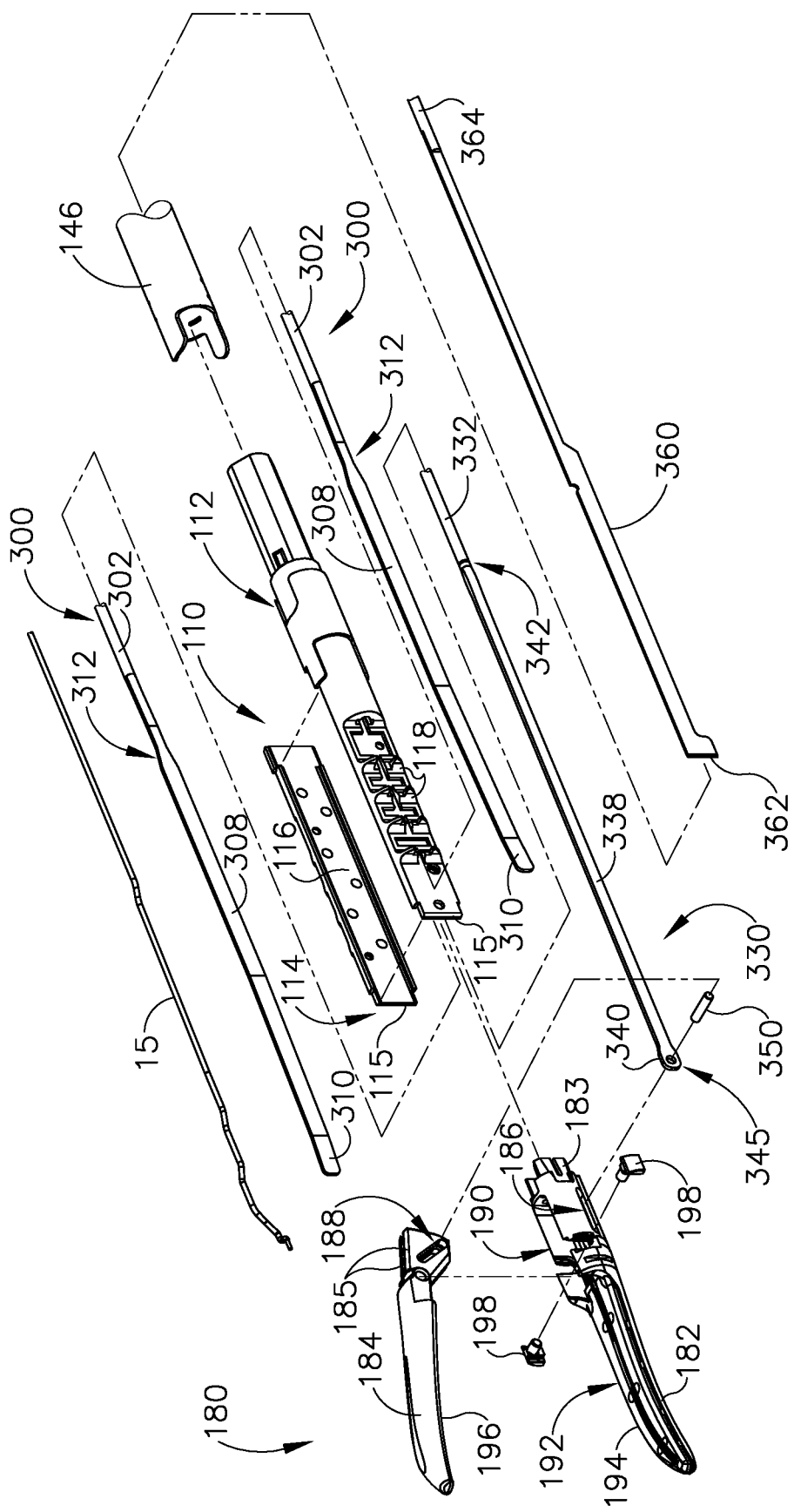
FIG. 3 depicts an exploded view of the articulation assembly and end effector of FIG. 2.
Figure 6:
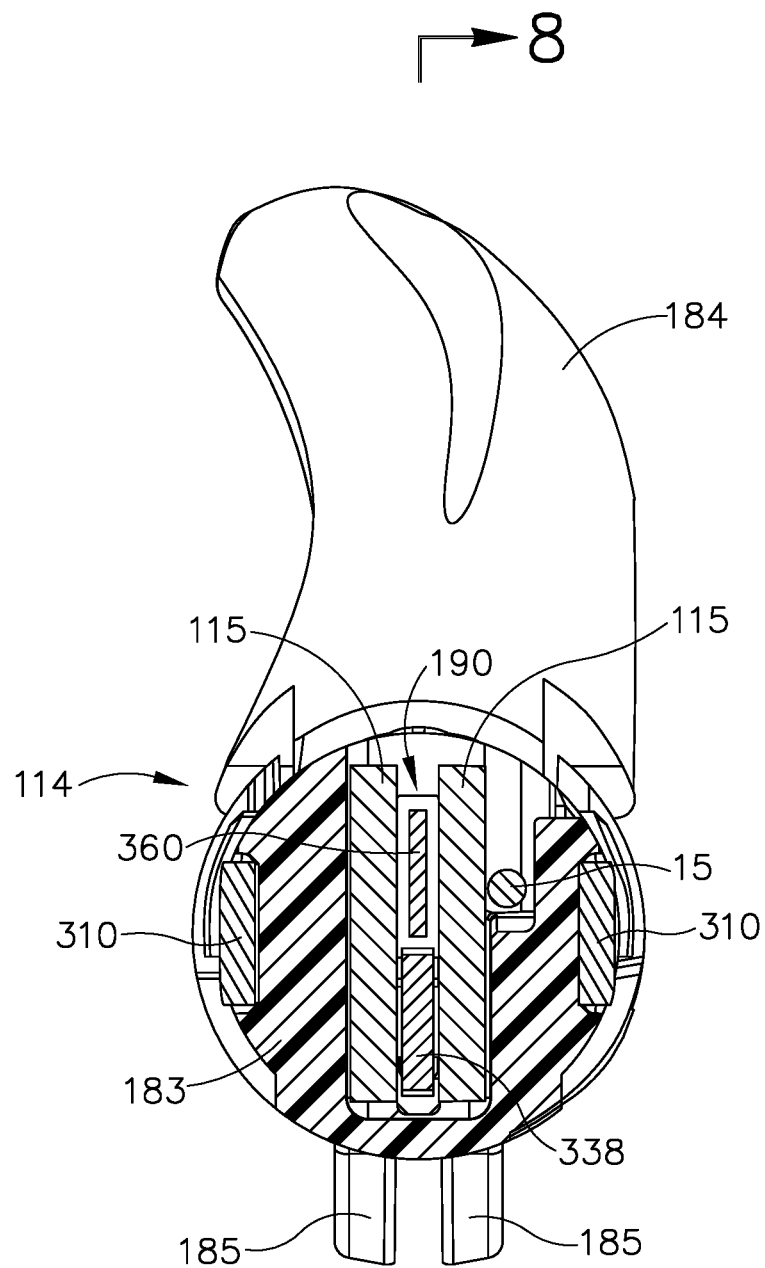
FIG. 6 depicts a cross-sectional rear view of the end effector of FIG. 2, taken along line 6-6 of FIG. 2.

FIGS. 2-3 show end effector (180), articulation assembly (110), and a distal portion (142) of shaft assembly (140). Articulation section (110) extends from a rigid proximal portion (112) to a distal portion (114). Rigid proximal portion (112) is fixed to outer sheath (146) of distal portion (142) of shaft assembly (140). As best seen in FIG. 6, distal portion (114) of articulation section (110) includes distal projections (115) inserted within the confines of proximal body (183) of lower jaw (182). A flexible member (116) extends from the distal end of rigid proximal portion (112) toward distal portion (114). As seen in FIG. 3, in the present example, two flexible members (116) are laterally coupled with each other such that both flexible members (116) extend along the same longitudinal axis. However, any other suitable combination or assembly of flexible members (116) may be used as would be apparent to one having ordinary skill in the art in view of the teachings herein.

Flexible members (116) include a plurality of guide members (118) that are configured to slidingly receive a band portion (308) of articulation connector (300). Flexible members (116) and band portions (308) are sufficiently flexible to bend relative to the longitudinal axis defined by shaft assembly (140) (as shown in FIGS. 10B-10C). As best seen in FIGS. 2 and 6, distal coupling portion (310) of articulation connector (300) is fixed to proximal body (183) of a lower jaw (182). As will be described in greater detail below, translation of articulation connectors (300) will drive deflection of end effector (180) relative to the longitudinal axis defined by shaft assembly (140).

Figure 5:
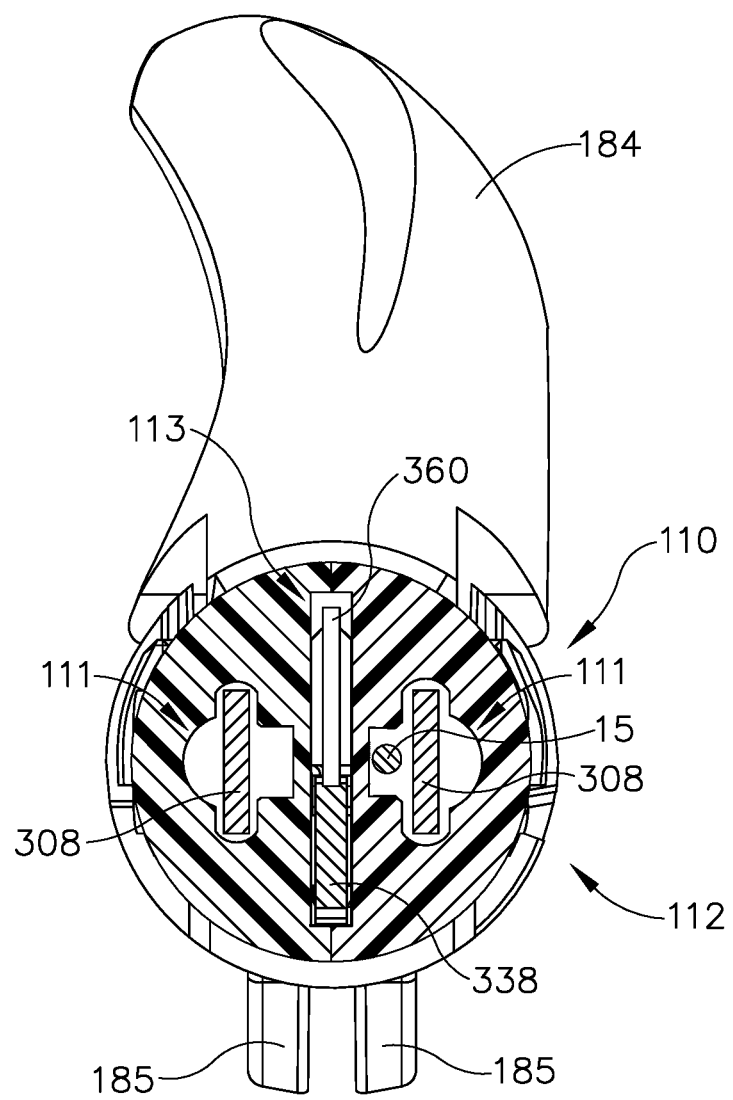
FIG. 5 depicts a cross-sectional rear view of the articulation assembly of FIG. 2, taken along line 5-5 of FIG. 2.

As shown in FIG. 5, rigid proximal portion (112) of articulation section (110) defines a pair of laterally offset pathways (111) and a central pathway (113). Laterally offset pathways (111) are dimensioned to slidably house corresponding band portions (308) of articulation connector (300) and electrical coupling (15); while central pathway (113) is dimensioned to slidably house corresponding portions of knife member (360) and band portion (338) of jaw closure connector (330). Central pathway (313) extends through flexible member (316) and proximal portion (314) to provide a pathway for knife member (360) and band portion (338) of jaw closure connector (330) from shaft assembly (140) to end effector (180). Therefore, knife member (360) and band portion (338) of jaw closure connector (330) are both sufficiently flexible to bend relative to the longitudinal axis defined by shaft assembly (140) (as shown in FIGS. 10B-10C).

As best seen in FIGS. 2-3 and 8A-8C, end effector (180) includes lower jaw (182) pivotally coupled with an upper jaw (184) via pivot couplings (198). Lower jaw (182) includes a proximal body (183) defining a slot (186), while upper jaw (184) includes proximal arms (185) defining a slot (188). Lower jaw (182) also defines a central channel (190) that is configured to receive proximal arms (185) of upper jaw (184), portions of knife member (360), band portion (338) of jaw closure connecter (330), and pin (350). Slots (186, 188) each slidably receive pin (350), which is attached to a distal coupling portion (340) of jaw closure connector (330). As will be described in greater detail below, jaw closure connector (330) is operable to translate within central channel (190) of lower jaw (182). Translation of jaw closure connector (330) drives pin (350). As will be described in greater detail below, because pin (350) is located within both slots (186, 188) and slots (186, 188) are angled relative to each other, pin (350) cams against proximal arms (185) to pivot upper jaw (184) toward and away from lower jaw (182) about pivot couplings (198). Therefore, upper jaw (184) is configured to pivot toward and away from lower jaw (182) about pivot couplings (198) to grasp tissue.

The term "pivot" does not necessarily require rotation about a fixed axis, but may include rotation about an axis that moves relative to end effector (180). Therefore, the axis at which upper jaw (184) pivots about lower jaw (182) may translate relative to both upper jaw (184) and lower jaw (182). Any suitable translation of the pivot axis may be used as would be apparent to one having ordinary skill in the art in view of the teachings herein.

Figure 8A:
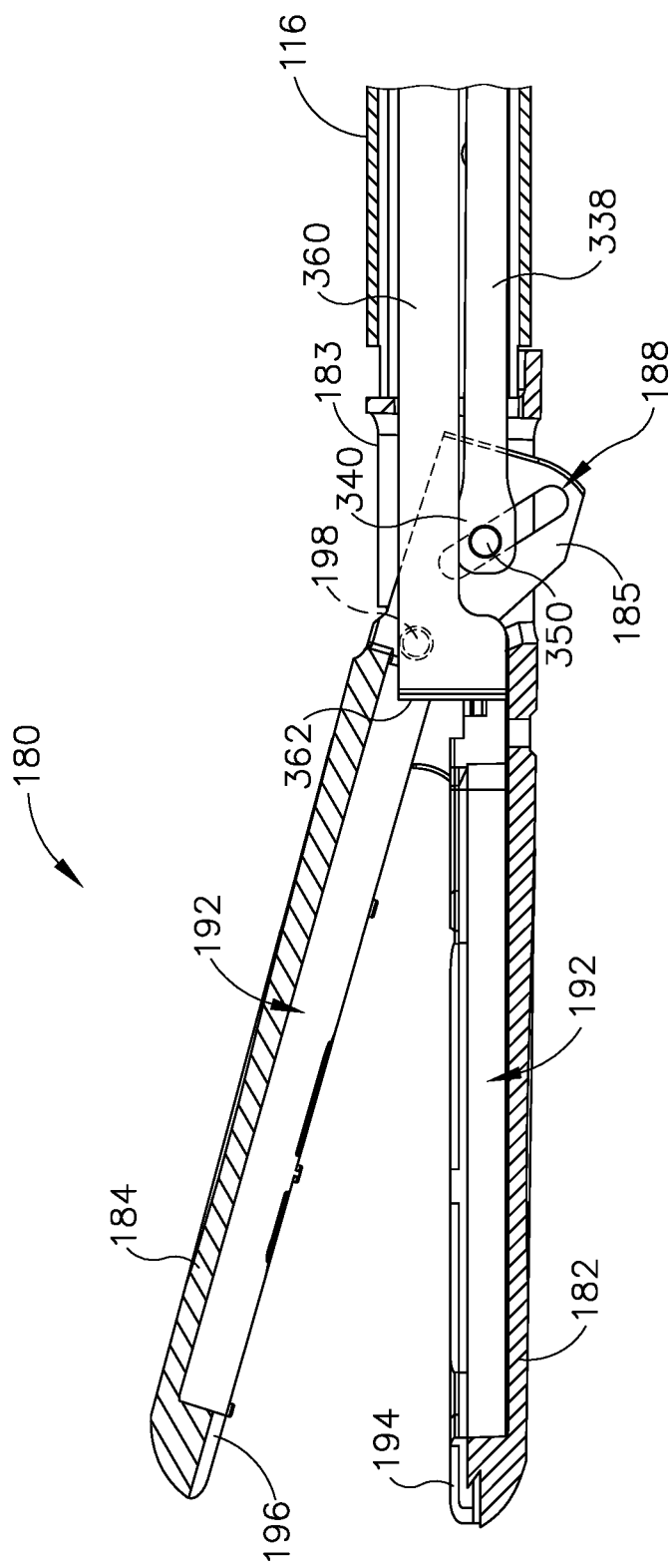
FIG. 8A depicts a cross-sectional side view of the end effector of FIG. 2, where the end effector is in the open and unfired state, taken along line 8-8 of FIG. 6.
Figure 8B:
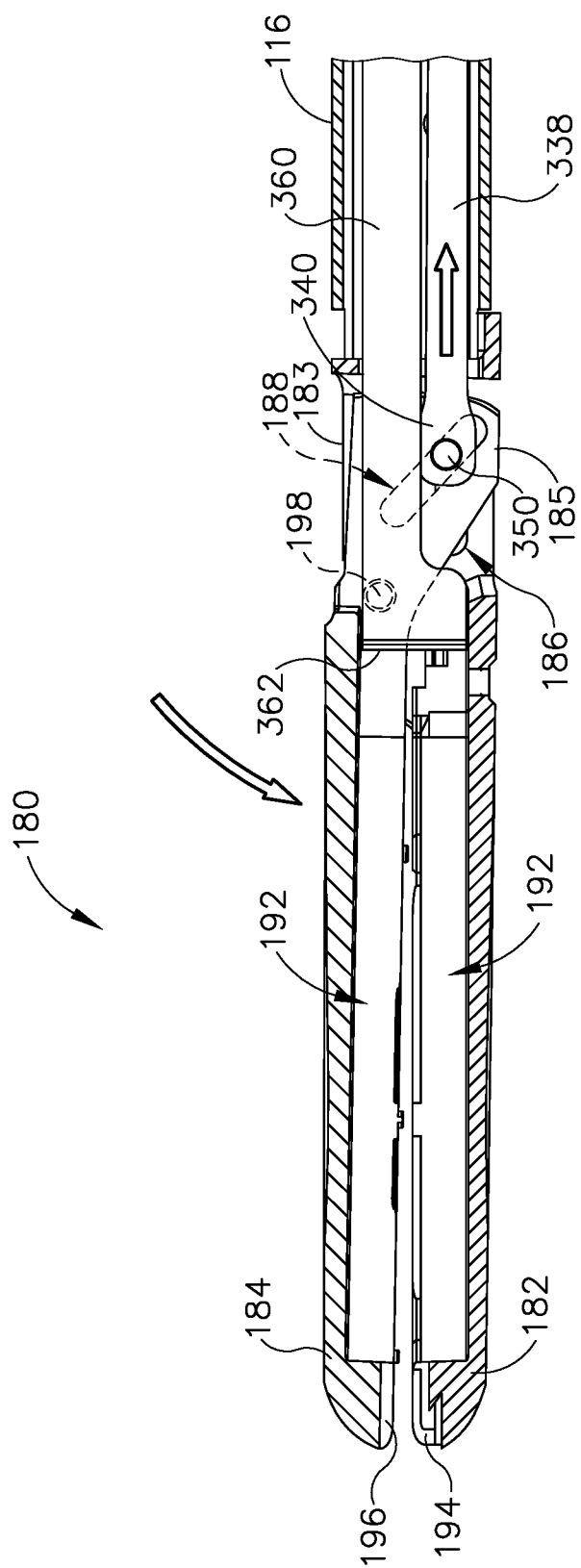
FIG. 8B depicts a cross-sectional side view of the end effector of FIG. 2, where the end effector is in the closed and unfired state, taken along line 8-8 of FIG. 6.
Figure 8C:
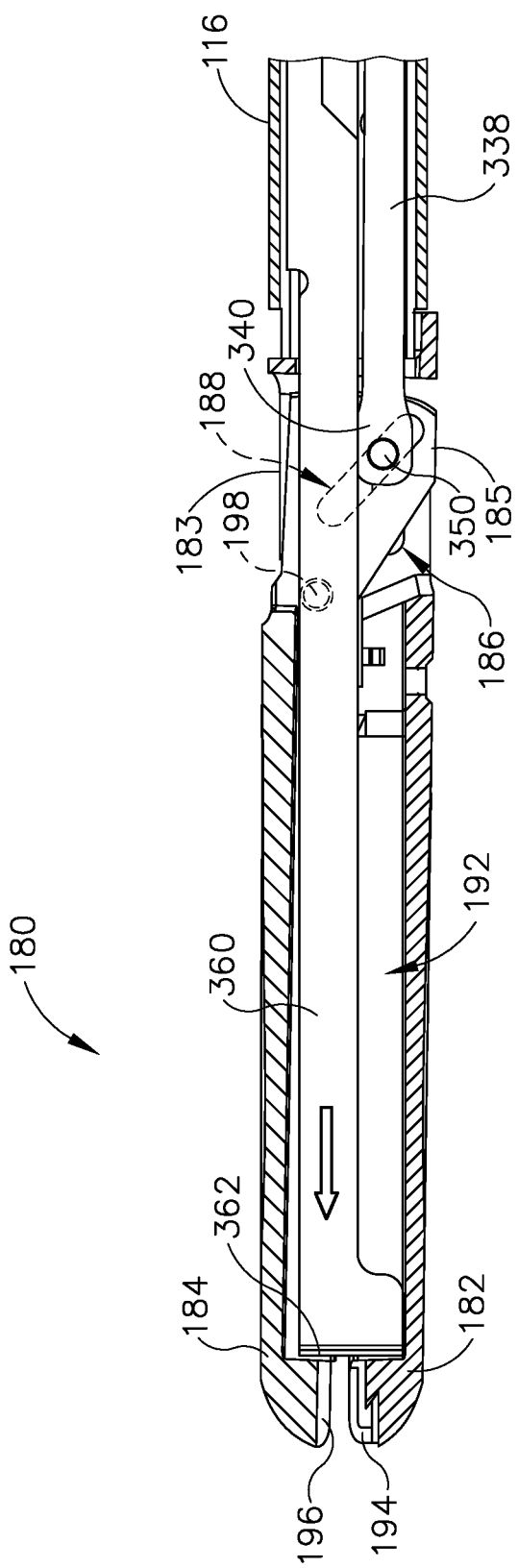
FIG. 8C depicts a cross-sectional side view of the end effector of FIG. 2, where the end effector is in the closed and fired state, taken along line 8-8 of FIG. 6.

Lower jaw (182) and upper jaw (184) also define a knife pathway (192). Knife pathway (192) is configured to slidingly receive knife member (360), such that knife member (360) may be retracted (as shown in FIGS. 8A-8B), and advanced (as shown in FIG. 8C), to cut tissue captured between jaws (182, 184). Lower jaw (182) and upper jaw (184) each comprise a respective electrode surface (194, 196). The power source may provide RF energy to electrode surfaces (194, 196) via electrical coupling (15) that extends through handle assembly (120), shaft assembly (140), articulation assembly (110), and electrically couples with one or both of electrode surfaces (194, 196). Electrical coupling (15) may selectively activate electrode surfaces (194, 196) in response to an operator pressing activation button (130).

FIGS. 7A-8C show an exemplary use of instrument (100) for end effector (180) to grasp, cut, and seal/weld tissue. As described above, and as shown between FIGS. 7A-7B and 8A-8B, jaw closure trigger (126) may be pivoted toward and away from pistol grip (124) and/or body (122) to open and close jaws (182, 184) of end effector (180) to grasp tissue. In particular, handle assembly (120) further includes a yoke (158) that is slidably coupled along proximal portion (144) of shaft assembly (140). Yoke (158) is coupled with rod portion (332) of jaw closure connector (330) such that translation of yoke (158) relative to proximal portion (144) of shaft assembly (140) translates rod portion (332) of jaw closure connector (330) relative to shaft assembly (140). However, rod portion (332) of jaw closure connector (330) is operable to rotate with proximal portion (144) of shaft assembly (140) relative to yoke (158), such that an operator may rotate knob (134) to rotate end effector (180) about the longitudinal axis defined by shaft assembly (140). In other words, rod portion (332) may rotate with shaft assembly (140), independently of yoke (158); yet rod portion (332) is longitudinally fixed with yoke (158). Any suitable coupling mechanism may be used as would be apparent to one having ordinary skill in the art in view of the teachings herein. For instance, yoke (158) may include an internal recess configured to allow rotation of a coupling member relative to yoke (158), while the internal recess of yoke (158) may abut against side walls of the coupling member to longitudinally drive rod portion (332).

As best seen in FIGS. 7A-7C, yoke (158) is coupled to a body (150) of jaw closure trigger (126) via a link (154). Link (154) is pivotally coupled with yoke (158) via pin (156); while link (154) is also pivotally coupled with body (150) of jaw closure trigger (126) via pin (152). Additionally, jaw closure trigger (126) is pivotally coupled with body (122) of handle assembly (120) via pin (170). Therefore, as shown between FIGS. 7A-7B, an operator may pull jaw closure trigger (126) toward pistol grip (124), thereby rotating jaw closure trigger (126) about pin (170). Rotation of jaw closure trigger (126) leads to rotation of link (154) about both pins (152, 156), which in turn drives yoke (158) in the proximal direction along proximal portion (144) of shaft assembly (140). As described above, jaw closure connector (330) extends within shaft assembly (140), articulation section (110), and central channel (190) of lower jaw (182). Additionally, jaw closure connector (330) is also attached to pin (350). Therefore, as seen between FIGS. 8A-8B, proximal translation of yoke (158) leads to proximal translation of pin (350), which in turn cams against slots (188) of proximal arms (185) of upper jaw (184), thereby rotating upper jaw (184) about pivot couplings (198) toward lower jaw (182) such that jaws (182, 184) achieve a closed configuration.

As best seen in FIGS. 7A-7B, yoke (158) is also coupled with a bias spring (155). Bias spring (155) is also coupled to a portion of body (122), such that bias spring (155) biases yoke (158) to the position shown in FIG. 7A (associated with the open configuration of end effector (180) as shown in FIG. 8A). Therefore, if an operator releases jaw closure trigger (126), bias spring (155) will translate yoke (158) to the position shown in FIG. 7A, thereby opening jaws (182, 184) of end effector (180).

As described above, and as shown between FIGS. 7B-7C and 8B-8C, knife trigger (128) may be pivoted toward and away from body (122) and/or pistol grip (124) to actuate knife member (360) within knife pathway (192) of jaws (182, 184) to cut tissue captured between jaws (182, 184). In particular, handle assembly (120) further includes a knife coupling body (174) that is slidably coupled along proximal portion (144) of shaft assembly (140). Knife coupling body (174) is coupled with knife rod (364) of knife member (360) such that translation of knife coupling body (174) relative to proximal portion (144) of shaft assembly (140) translates knife rod (364) and knife member (360) relative to shaft assembly (140). However, knife rod (364) of knife member (360) is operable to rotate with proximal portion (144) of shaft assembly (140) relative to knife coupling body (174), such that an operator may rotate knob (134) to rotate end effector (180) about the longitudinal axis defined by shaft assembly (140). In other words, knife rod (264) may rotate with shaft assembly (140), independently of knife coupling body (174); yet knife rod (264) is longitudinally fixed to knife coupling body (174). Any suitable coupling mechanism may be used as would be apparent to one having ordinary skill in the art in view of the teachings herein. For instance, knife coupling body (174) may include an internal recess that is configured to allow rotation of a coupling member relative to knife coupling body (174), while the internal recess of knife coupling body (174) may abut against side walls of the coupling member to longitudinally drive knife member (360).

As best seen in FIGS. 7B-7C, knife coupling body (174) is coupled to a second pivoting arm (168) via a protrusion (176) of the knife coupling body (174) and a slot (172) defined by second pivoting arm (168). Second pivoting arm (168) is pivotally coupled with body (122) of handle assembly (120) via pin (170). Second pivoting arm (168) is coupled to a first pivoting arm (160) via a protrusion (166) of second pivoting arm (168) and a slot (164) defined by first pivoting arm (160). First pivoting arm (160) is pivotally connected to a pin (162) and is unitarily attached to knife trigger (128). Therefore, as knife trigger (128) pivots toward body (122) and/or pistol grip (124), first pivoting arm (160) pivots about pin (162) in a first angular direction. As first pivoting arm (160) pivots about pin (162), second pivoting arm (168) pivots about pin (170) in a second, opposite, angular direction due to slot (164) actuating protrusion (166). As second pivoting arm (168) pivots about pin (170) in the second angular direction, knife coupling body (174) translates along proximal portion (144) of shaft assembly (140) due to slot (172) actuating protrusion (176) of knife coupling body (174). Because knife coupling body (174) is coupled to knife member (360), knife member (360) translates distally within shaft assembly (140), articulation section (110), and within knife pathway (192) of end effector (180), as best shown between FIGS. 8B-8C. Knife member (360) includes distal cutting edge (362) that is configured to sever tissue captured between jaws (182, 184). Therefore, pivoting knife trigger (128) causes knife member (360) to actuate within knife pathway (192) of end effector (180) to sever tissue captured between jaws (182, 184).

As best seen in FIGS. 7B-7C, knife trigger (128) is biased to the positions shown in FIG. 7A-7B by a bias arm (129). Bias arm (129) may include any suitable biasing mechanism as would be apparent to one having ordinary skill in the art in view of the teachings herein. For instance, bias arm (129) may include a torsion spring. Bias arm (129) is also coupled to a portion of body (122), such that bias arm (129) biases knife trigger (128) to the position shown in FIG. 7A-7B (associated with the knife member (360) in the retracted position). Therefore, if an operator releases knife trigger (128), bias arm (129) returns knife trigger (128) to the position shown in FIGS. 7A-7B, thereby translating knife member (360) toward the retracted position.

With distal cutting edge (362) of knife actuated to the advance position (position shown in FIG. 8C), an operator may press activation button (130) to selectively activate electrode surfaces (194, 196) of jaws (182, 184) to weld/seal severed tissue that is captured between jaws (182, 184).

As described above, and as best shown between FIGS. 9A-10C, rotation of articulation control (132) relative to body (122) of hand assembly (120) will drive deflection of end effector (180) from the longitudinal axis defined by shaft assembly (140) from a non-articulated configuration (FIG. 10A) to an articulated configuration (FIGS. 10B-10C). In particular, as best shown in FIGS. 9A-9C, handle assembly (120) further includes an articulation drive assembly (200). Articulation drive assembly (200) includes a rotatable housing (220) that is unitarily connected to articulation control (132), such that rotation of articulation control (132) relative to body (122) leads to rotation of rotatable housing (220) relative to body (122). Half of rotatable housing (220) is purposely omitted from FIGS. 9A-9C for purposes of clarity.

Rotatable housing (220) and articulation control (132) are rotatably coupled to a distal cap (202) and a proximal cap (210), which are both fixed to body (122) of handle assembly (120). Rotatable housing (220) includes a first internal threading (222) and a second internal threading (224). First internal threading (222) is threaded in an opposite orientation/direction as compared to second internal threading (224).

Additionally, articulation drive assembly (200) includes a first lead screw (230) and a second lead screw (250) slidably coupled along proximal portion (144) of shaft assembly (140). First lead screw (230) and second lead screw (250) each have pins (204) extending through them. Pins (204) are fixed to proximal cap (210) and distal cap (202). Therefore, pins (204) are rotationally fixed relative to body (122) of handle assembly (120). Because pins (204) extend through lead screws (230, 250), lead screws (230, 250) are also rotationally fixed relative to body (122) of handle assembly (120). However, first lead screw (230) and second lead screw (250) are slidably attached to pins (204). Therefore, lead screws (230, 250) may translate, without rotating, along pins (204) and proximal portion (144) of shaft assembly (140) within the confines of rotatable housing (220).

First lead screw (230) includes threading (232) that is configured to complementary mesh with first internal threading (222) of rotatable housing (220). Second lead screw (250) includes threading (252) that is configured to complementary mesh with second internal threading (224) of rotatable housing (220). Because lead screws (230, 250) are rotationally fixed relative to body (122), and because each lead screw (230, 250) has threading (232, 252) that meshes with internal threading (222, 224) having opposing orientations/direction, rotation of rotatable housing (220) in one direction leads to simultaneous translation of lead screws (230, 250) in opposing longitudinal directions. In other words, rotation of rotatable housing (220) causes first and second internal threading (222, 224) to cam against threading (232, 252) of lead screws (230, 250) respectively, such that longitudinal actuating lead screws (230, 250) in opposite longitudinal directions. For instance, if an operator rotates articulation control (132) and rotatable housing (220) in a first rotational direction, lead screws (230, 250) will translate away from each other (as shown between FIGS. 9A-9B) due to rotation of internal threading (222, 224) causing contact with threading (232, 252) of lead screws (230, 250), respectively. However, if an operator rotates articulation control (132) and rotatable housing (220) in a second rotational direction, lead screws (230, 250) will translate toward each other (as shown between FIGS. 9A and 9C) due to rotation of internal threading (222, 224) causing contact with threading (232, 252) of lead screws (230, 250), respectively.

Each lead screw (230, 250) is coupled with a respective rod portion (302) of articulation connectors (300) such that translation of lead screws (230, 250) relative to proximal portion (144) of shaft assembly (140) translates rod portions (302) of articulation connectors (300) relative to shaft assembly (140). However, rod portions (302) of articulation connectors (300) are operable to rotate with proximal portion (144) of shaft assembly (140) relative to their respective lead screws (230, 250), such that an operator may rotate knob (134) to rotate end effector (180) about the longitudinal axis defined by shaft assembly (140). In other words, articulation connectors (300) may rotate with shaft assembly (140) independently of lead screws (230, 250), yet articulation connectors (300) are longitudinally fixed with lead screws (230). Any suitable coupling mechanism may be used as would be apparent to one having ordinary skill in the art in view of the teachings herein. For instance, lead screws (230, 250) may each include an internal recess configured to allow rotation of a coupling member relative to lead screws (230, 250), while the internal recess of lead screws (230, 250) may abut against side walls of the coupling member to longitudinally drive articulation connection (300).

As mentioned above, articulation connector (300) includes rod portions (302) that are configured to longitudinally translate relative to shaft assembly (140) by coupling with lead screws (230, 250). As also described above, each articulation connector (300) include a flexible band portion (308) slidably disposed within articulation section (110) of instrument (100); while articulation connectors (300) each include a distal coupling portion (310) fixed to proximal body (183) of lower jaw (182). Distal coupling portion (310) may be fixed to proximal body (183) of lower jaw (182) through any suitable means known to a person having ordinary skill in the art in view of the teachings herein, such as welding. As also mentioned above, articulation section (110) also includes flexible members (116) that are configured to bend relative to the longitudinal axis defined by the shaft assembly (140) to allow end effector (180) to deflect relative to the longitudinal axis defined by shaft assembly (140).

In an exemplary use, an operator may rotate articulation control (132) and rotatable housing (220) in a first rotational direction such that lead screws (230, 250) translate away from each other (as shown between FIGS. 9A-9B). Because lead screws (230, 250) are each coupled to a respective articulation connector (300), each articulation connector (300) translates with its respective lead screw (230, 250). Therefore, articulation connectors (300) translate in opposing directions in response to rotation of articulation control (131) and rotatable housing (220). As described above, articulation connectors (300) are attached to proximal body (183) of lower jaw (182) via distal coupling portions (310). In particular, distal coupling portion (310) of each articulation connector (300) is attached to an opposite side of proximal body (183) of lower jaw (182).

As best shown in FIG. 10B, opposing translation of articulation connectors (300) causes one articulation connector (300) to drive end effector (180) proximally, while causing another articulation connector (300) drive end effector (180) distally, thereby articulating end effector (180) and flexible member (116) of articulation section (110) to a first articulated configuration. Band portion (348) and portions of knife member (360) within central pathway (113) are also flexible to bend with flexible member (116). The degree to which end effector (180) articulates relative to the longitudinal axis defined by shaft assembly (140) may be determined by the longitudinal distance lead screws (230, 250) travel away from each other compared to their positions shown in FIG. 9A. Therefore, an operator may choose the degree at which end effector (180) articulates based on the rotational displacement of articulation control (132) from its home position shown in FIG. 9A.

Additionally, an operator may rotate articulation control (132) and rotatable housing (220) in a second rotational direction such that lead screws (230, 250) translate toward each other (as shown between FIGS. 9A and 9C). Because lead screws (230, 250) are each coupled to a respective articulation connector (300), each articulation connector (300) translates with its respective lead screw (230, 250). Therefore, articulation connectors (300) translate in opposing directions. As best shown in FIG. 10C, translation of articulation connectors (300) leads to end effector (180) being driven to a second articulated configuration. As described above, articulation connectors (300) are attached to a proximal body (183) of lower jaw (182) via distal coupling portions (310). In particular, distal coupling portion (310) of each articulation connector (300) is attached to an opposite side of proximal body (183) of lower jaw (182).

As best shown in FIG. 10C, opposing translation of articulation connectors (300) causes one articulation connector (300) to drive end effector (180) proximally, while causing another articulation connector (300) to drive end effector (180) distally, thereby articulating end effector (180) and flexible member (116) of articulation section (110) to a first articulated configuration.

II. Exemplary Articulation Drive Assembly with Tactile/Audible Feedback

Figure 10A:
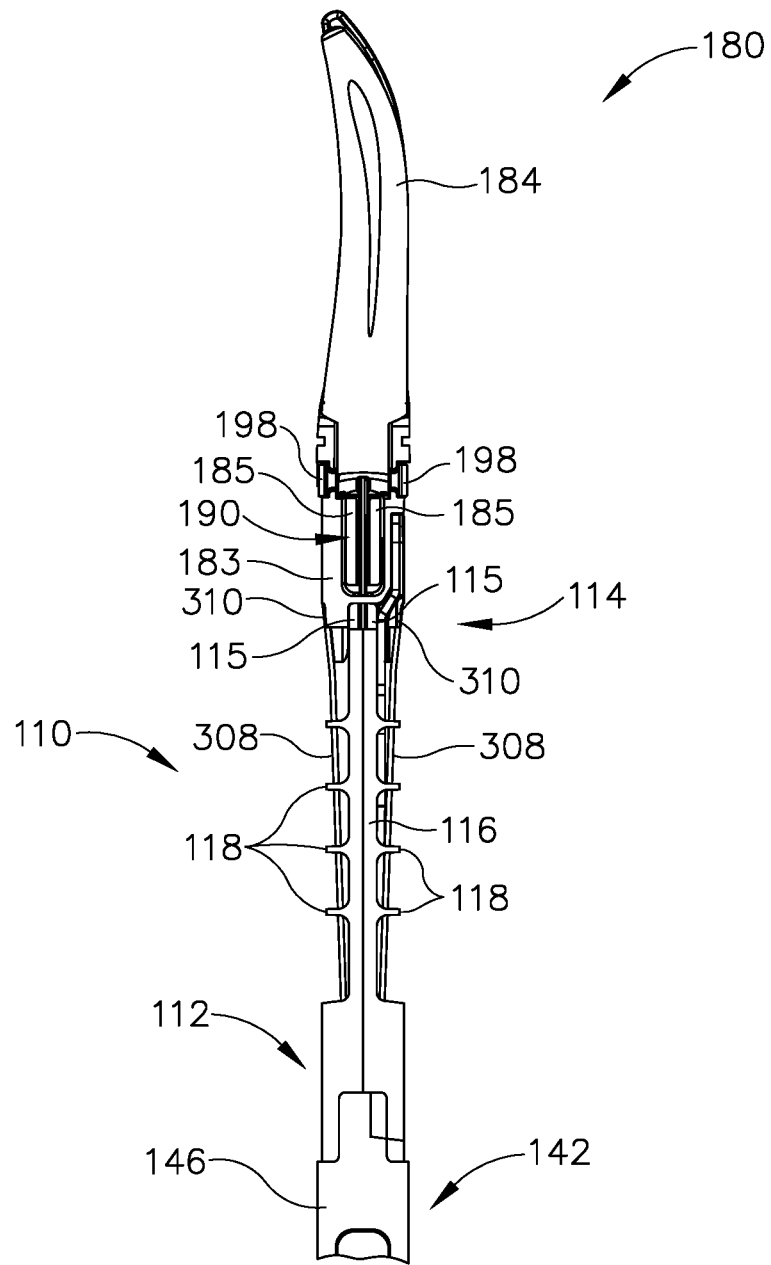
FIG. 10A depicts a top plan view of the end effector and articulation assembly of FIG. 2, where the articulation assembly is in the non-articulated configuration.
Figure 10B:
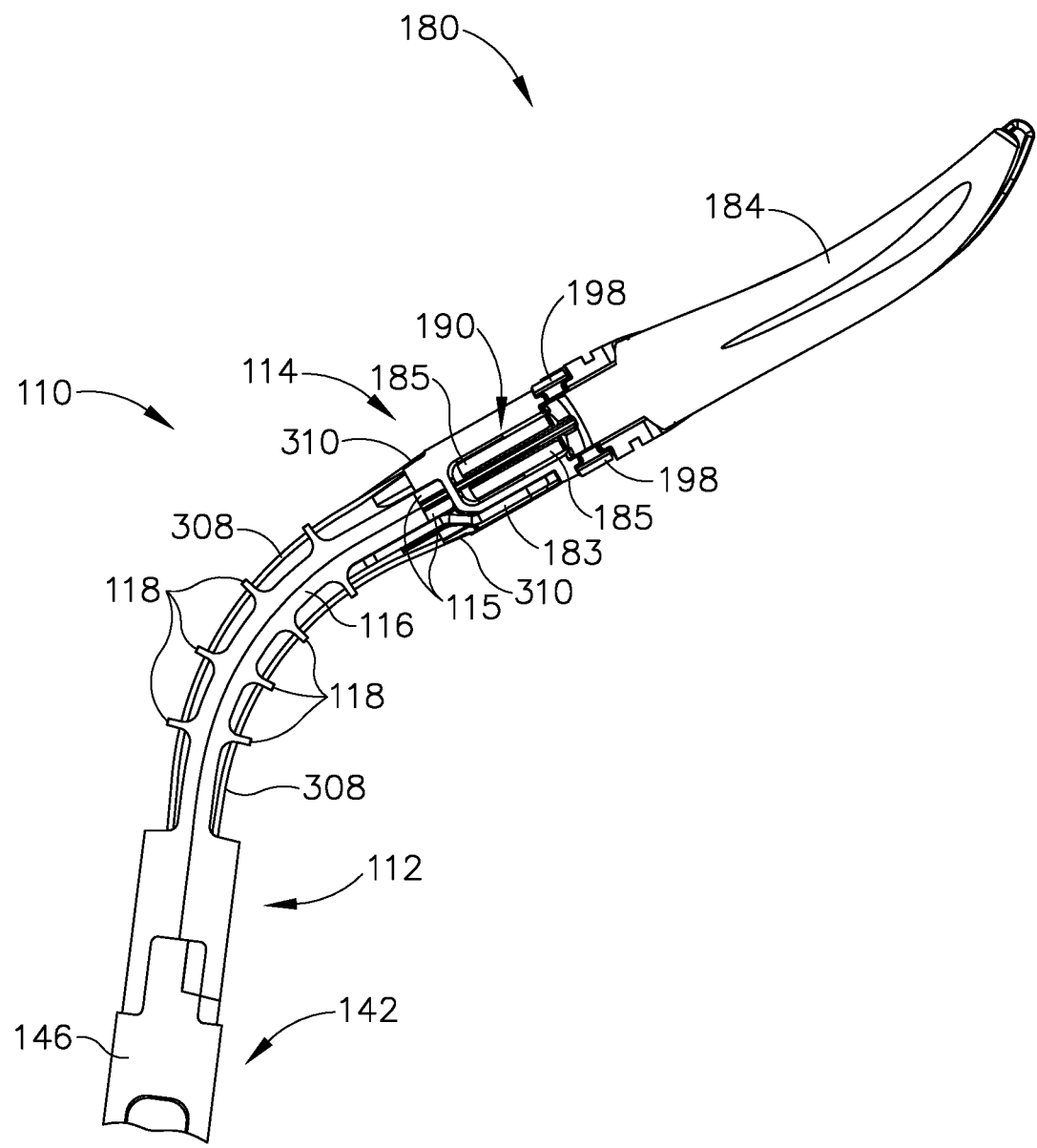
FIG. 10B depicts a top plan view of the end effector and articulation assembly of FIG. 2, where the articulation assembly is in the first articulated configuration.
Figure 10C:
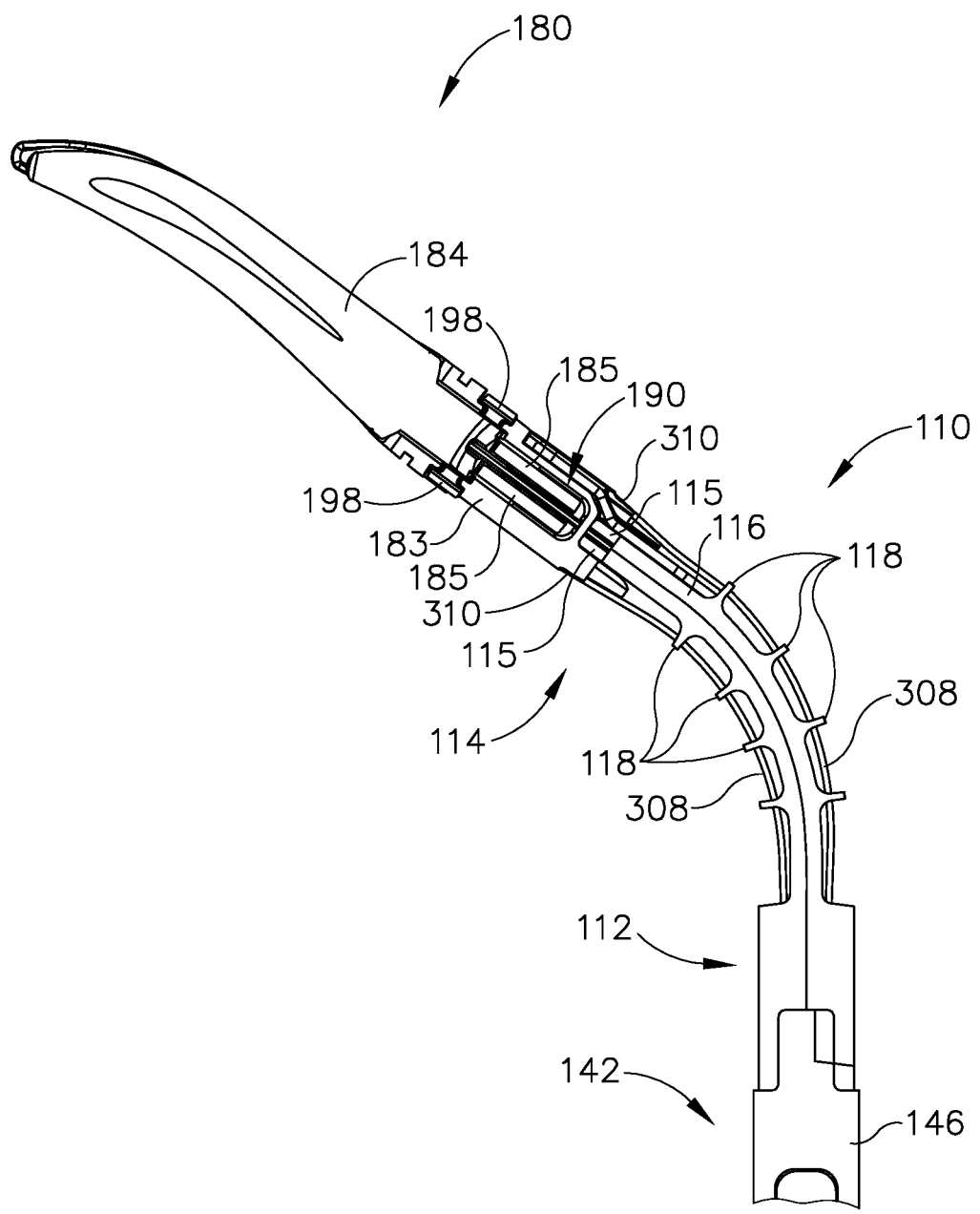
FIG. 10C depicts a top plan view of the end effector and articulation assembly of FIG. 2, where the articulation assembly is in the second articulated configuration.
Figure 11:
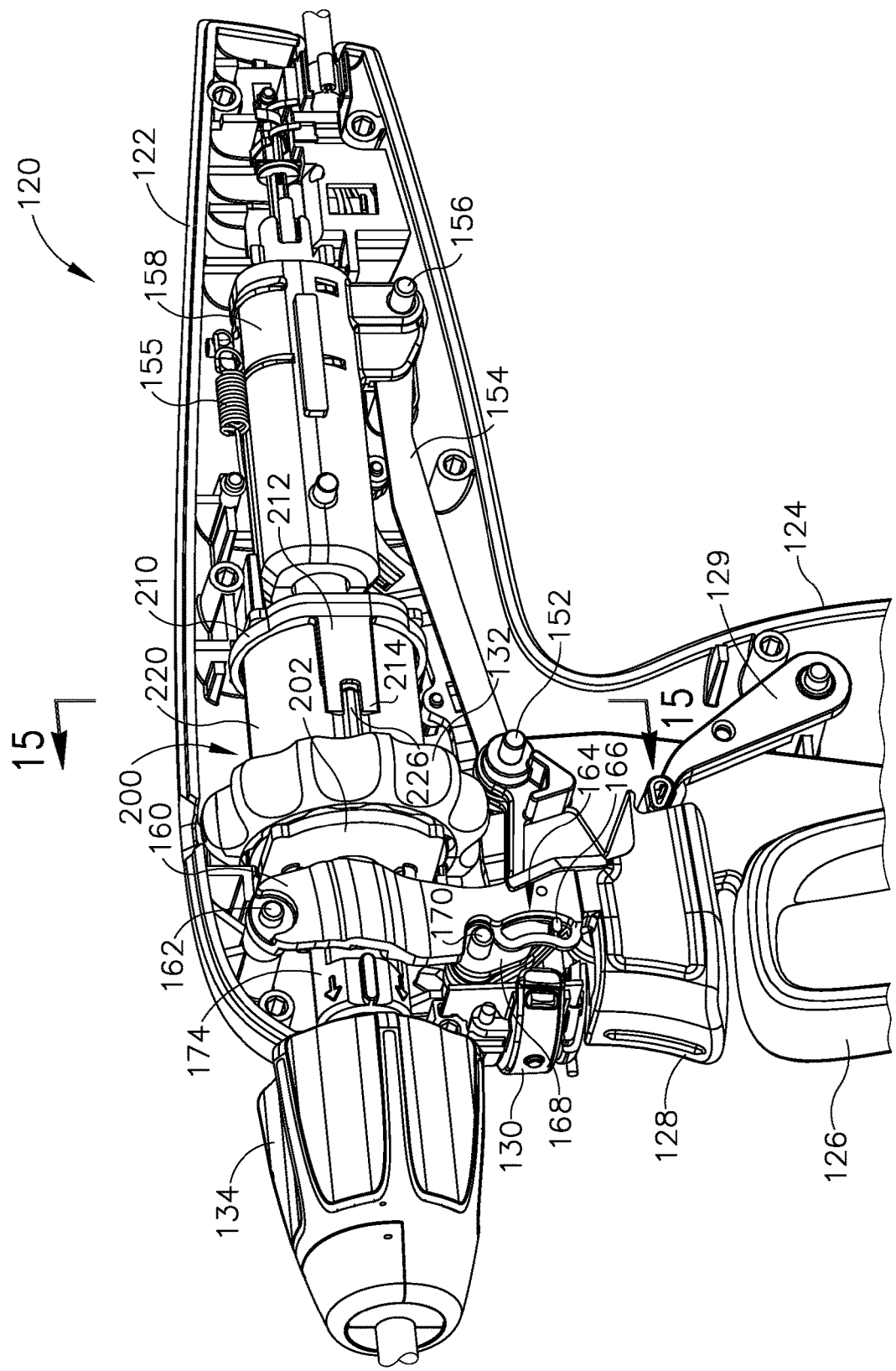
FIG. 11 depicts another perspective view of the handle assembly of FIG. 7A, with selected portions omitted for purposes of clarity.
Figure 12:
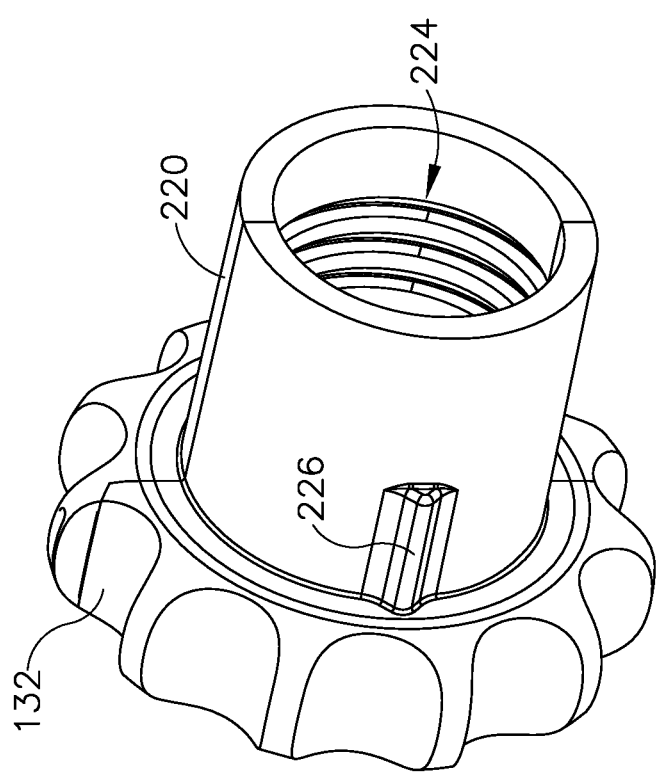
FIG. 12 depicts a perspective view of a rotatable housing of an articulation drive assembly of the handle assembly of FIG. 7A.

In some instances, it may be difficult for an operator to determine when end effector (180) and articulation assembly (110) are in the non-articulated configuration (as shown in FIG. 10A). For instance, during a procedure, an operator may insert end effector (180), articulation assembly (110), and a distal end of shaft assembly (140) into a patient via a pathway provided by a trocar, while end effector (180) and articulation assembly (110) are in the non-articulated configuration. After end effector (180), articulation assembly (110), and the distal end of shaft assembly (140) are inserted into a patient, the operator may deflect end effector (180) relative to the longitudinal axis defined by shaft assembly (140) via articulation control (132) as described above. After end effector (180) has been moved to an articulated configuration, it may be necessary to return end effector (180) to the non-articulated configuration before removing end effector (180) from the patient via the trocar. Even with visual confirmation, the operator may believe that end effector (180) is in the non-articulated configuration, but in reality, end effector (180) may be partially articulated. Alternatively, end effector (180) may in fact be in the non-articulated configuration when an operator begins to remove end effector (180), but may accidentally deflect to an articulated position via accidental rotation of articulation control (132).

Removing a partially articulated end effector (180) from a patient may cause inadvertent consequences. For example, when removing end effector (180) from the pathway provided by the trocar, the operator may accidentally cause contact between a partially articulated end effector (180) and the trocar such that the trocar is accidentally moved relative to the patient. Such contact may misalign the trocar, or even completely remove the trocar from the patient. Therefore, it may be desirable to more readily enable the operator to confirm that end effector (180) is in the non-articulated configuration before attempting to remove end effector (180) from a patient via the pathway provided by the trocar.

FIGS. 11-15C show how articulation drive assembly (200) of the present example includes a detent feature that is configured to allow an operator to readily confirm if end effector (180) is in the non-articulated configuration (as shown in FIG. 10A). In particular, proximal cap (210) of articulation drive assembly (200) includes a cantilever arm (212) extending distally from cap (210), and terminating into two camming projections (214) defining an open slot (216). Additionally, rotatable housing (220) includes a radially protruding ridge (226). As will be described in greater detail below, radially protruding ridge (226) is configured to interact with camming projections (214) to deflect cantilever arm (212) while rotatable housing (220) is driving end effector (180) toward and away from the non-articulated configuration. The interaction between radially protruding ridge (226) and cantilever arm (212) may provide resistive, tactile, and/or audible feedback to an operator when end effector (180) is driven toward and away from the non-articulated configuration.

As described above rotatable housing (220) is unitarily connected to articulation control (132). Therefore, as an operator rotates rotatable housing (220) relative to body (122) via articulation control (132), radially protruding ridge (226) also rotates with rotatable housing (220) relative to body (122). Radially protruding ridge (226) is positioned along an exterior of rotatable housing (220) in order to fit within open slot (216) defined by camming projections (214) when end effector (180) is in the non-articulated configuration. Additionally, a portion of radially protruding ridge (226) is directly adjacent to camming projections (214) when protruding ridge (226) is housed within open slot (216). Therefore, radially protruding ridge (226) is placed along the exterior of rotatable housing (220) to selectively interact with camming projections (214) when rotatable housing (220) drives articulation toward and away from the non-articulated configuration as described above. Radially protruding ridge (226) may have gradual radial contour around an exterior portion of ratable housing (220). This gradual contour may help radially protruding ridge (225) of rotatable housing (220) interact with camming projections (214) as described in greater detail below. In some variations, radially protruding ridge (226) has an obliquely angled slope rather than a gradual radial contour.

Figure 13:
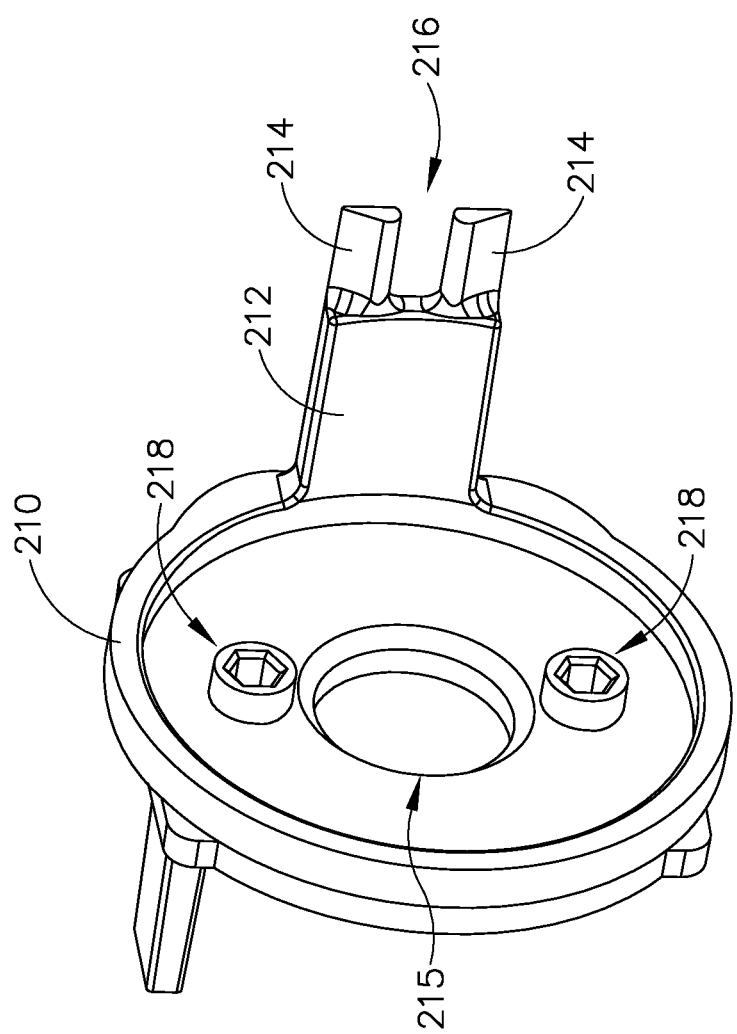
FIG. 13 depicts a perspective view of a proximal cap of the articulation drive assembly of the handle assembly of FIG. 7A.

As best seen in FIG. 13, proximal cap (210) defines a shaft through hole (215) that is configured to receive proximal portion (144) of shaft assembly (140). Additionally, proximal cap (210) defines pin holes (218) that are configured to receive pins (204) to rotationally fix lead screws (230, 250) relative to proximal cap (210). As described above, proximal cap (210) is fixed to body (122) of handle assembly (120). Therefore, as rotatable housing (220) and radially protruding ridge (226) rotate relative to body (122), rotatable housing (220) and radially protruding ridge (226) also rotate relative to proximal cap (210).

Cantilever arm (212) extends distally from proximal cap (210) such that cantilever arm (212) does not contact rotatable housing (220) when proximal cap (210) is properly coupled with housing (220), regardless of the rotational position of housing (220) relative to proximal cap (210). Camming projections (214) extend distally from cantilever arm (212) such that camming projections (214) contact radially protruding ridge (226) when ridge (226) rotates underneath camming projections (214). Additionally, cantilever arm (212) and/or camming projections (214) are sufficiently resilient such that as radially protruding ridge (226) cams against camming projections (214), cantilever arm (212) and/or camming projections (214) may deflect from a natural position to a flexed position relative to the rest of proximal cap (210). When radially protruding ridge (226) no longer cams against camming projections (214), cantilever arm (212) and camming projections (214) return from the flexed position to the natural position. As will be described in greater detail below, the resilient nature of cantilever arm (212) and/or camming projections (214) may provide resistive/tactile/audible feedback when radially protruding ridge (226) rotates within or out of open slot (216) defined by camming projections (214).

Figure 14A:
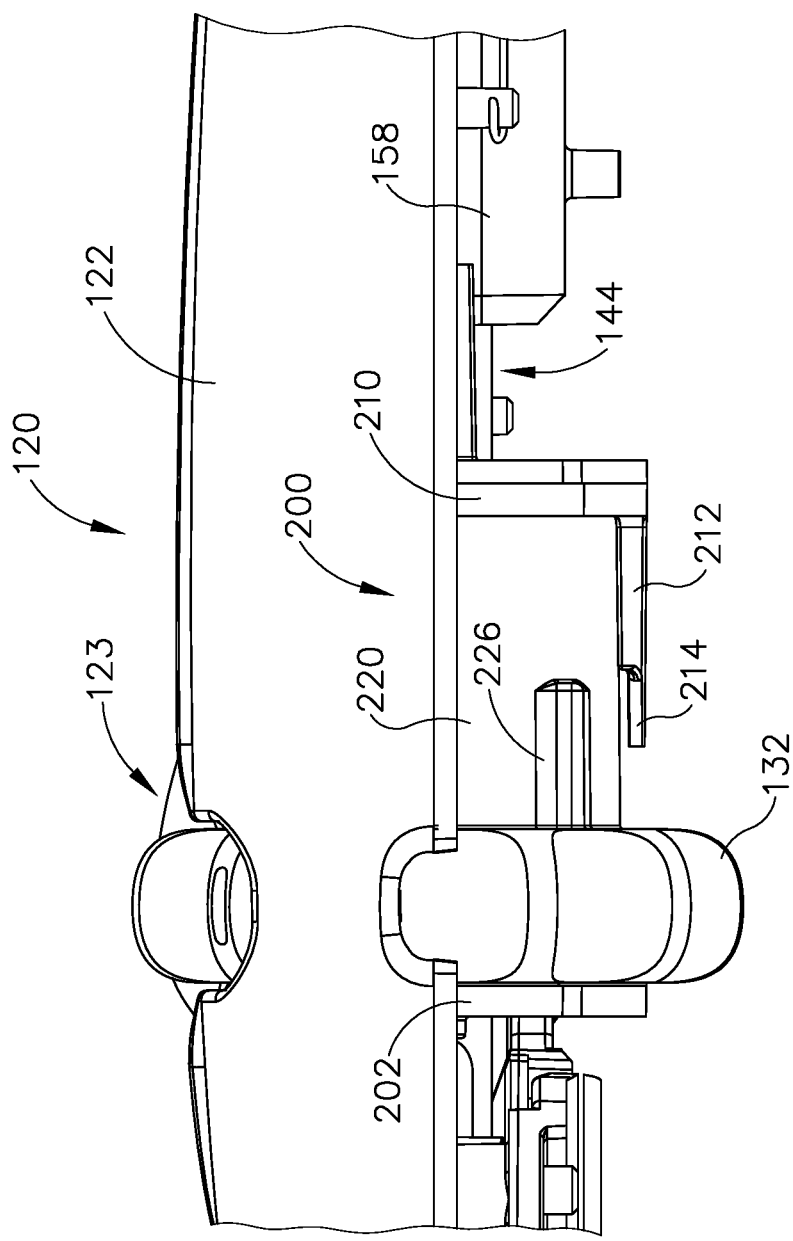
FIG. 14A depicts a top plan view of the handle assembly of FIG. 7A, with a portion of the handle assembly omitted, where the rotatable housing of FIG. 12 is rotated to a first rotational position relative to the proximal cap of FIG. 13, where the first rotational position of the rotatable housing corresponds to the articulation assembly of FIG. 3 in an articulated configuration.

FIGS. 14A-15C show an exemplary use of articulation drive assembly (200) to confirm that articulation section (110) and end effector (180) are in the non-articulated configuration. FIGS. 14A-14C show handle assembly (120) with a portion of body (122) omitted for purposes of clarity. FIGS. 14A and 15A show rotatable housing (220) rotated to a position corresponding with articulation section (110) and end effector (180) in an articulated configuration. At the stage depicted in FIGS. 14A and 15A, housing (220) is positioned such that radially protruding ridge (226) is not in contact with camming projections (214) and is not within the confines of open slot (216).

Figure 14B:
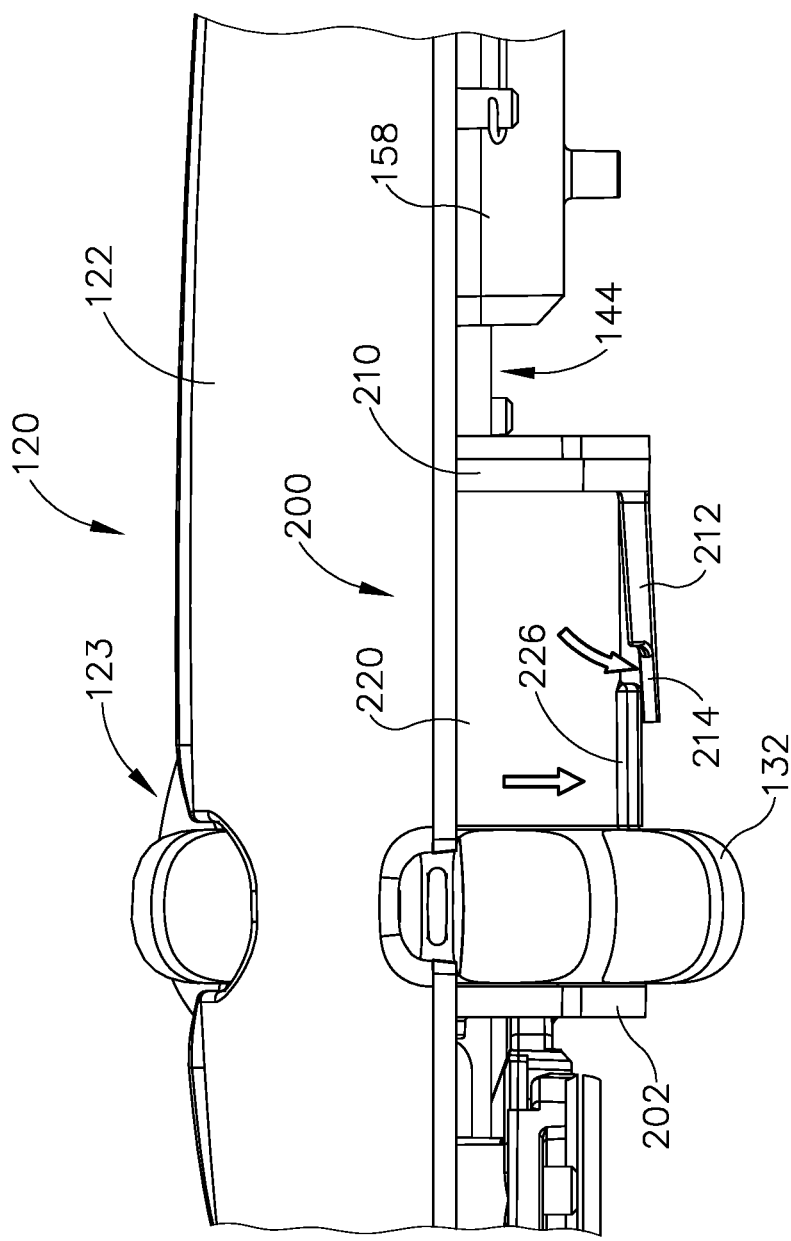
FIG. 14B depicts a top plan view of the handle assembly of FIG. 7A, with a portion of the handle assembly omitted, where the rotatable housing of FIG. 12 is rotated to a second rotational position relative to the proximal cap of FIG. 13, where the second rotational position of the rotatable housing corresponds to the articulation assembly of FIG. 3 in an articulated configuration.
Figure 15A:
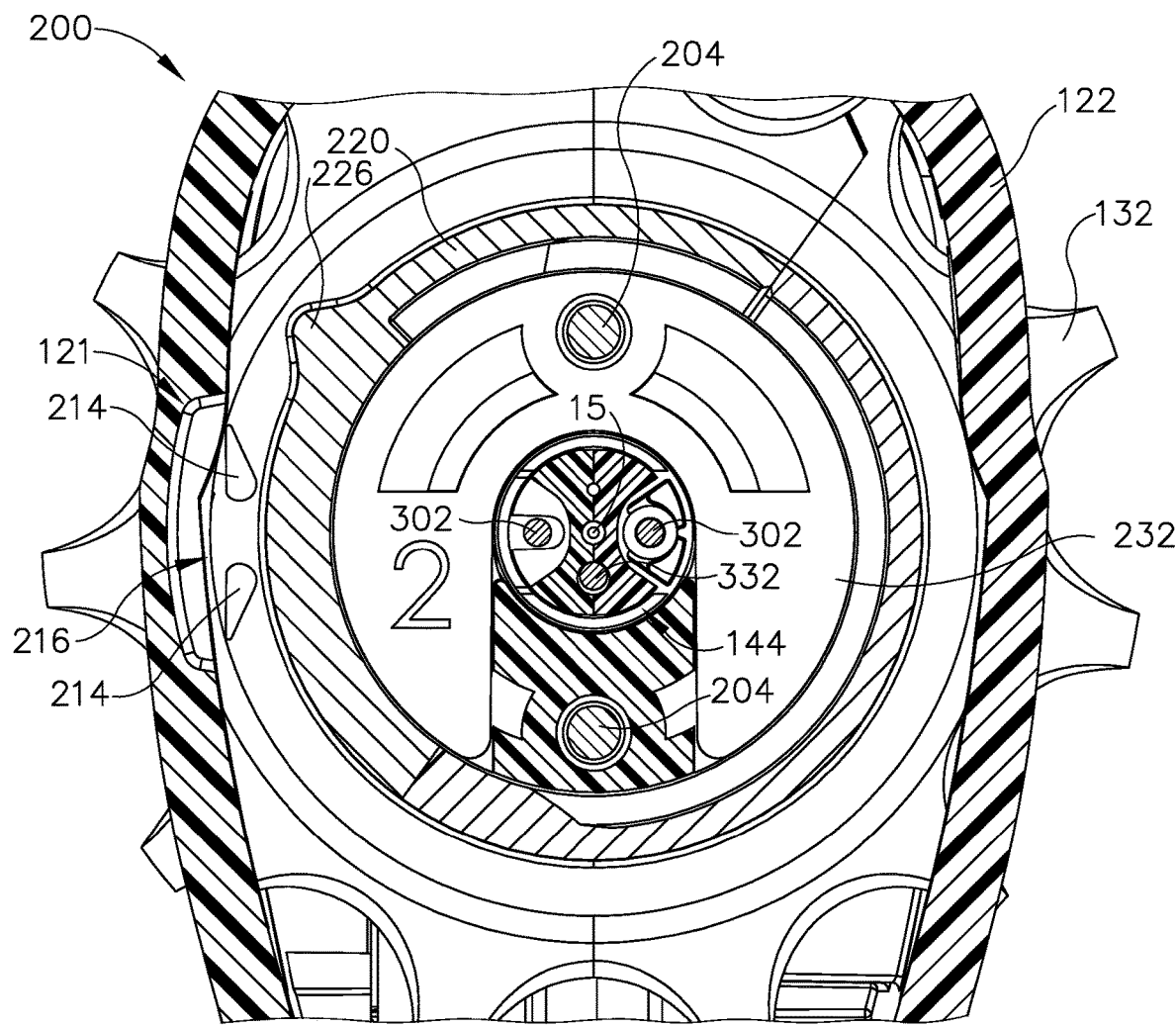
FIG. 15A depicts a cross-sectional rear view of the handle assembly of FIG. 7A, where the rotatable housing of FIG. 12 is rotated to the first rotational position relative to the proximal cap of FIG. 13, where the first rotational position of the rotatable housing corresponds to the articulation assembly of FIG. 3 in an articulated configuration, taken along line 15-15 of FIG. 11.
Figure 15B:
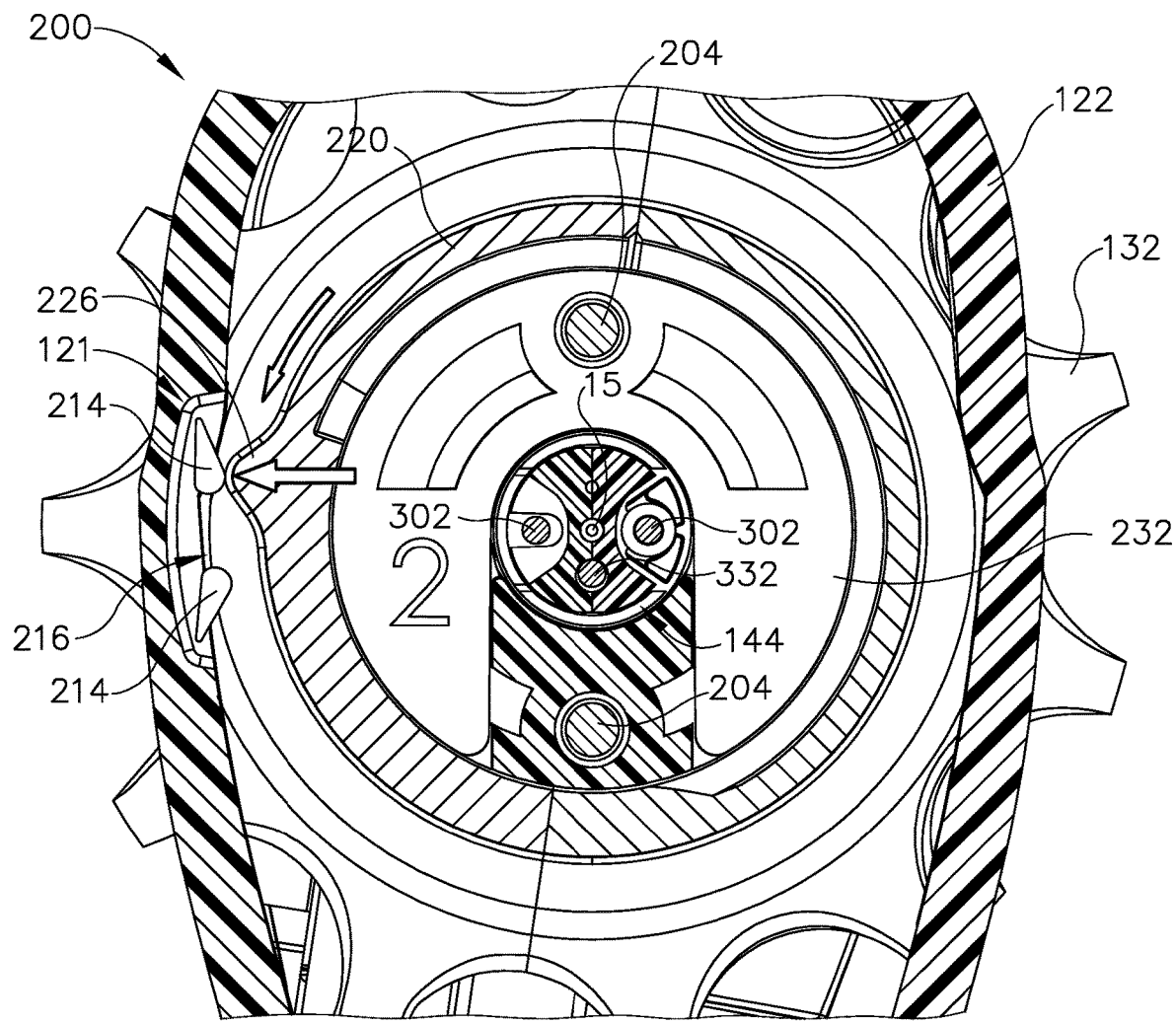
FIG. 15B depicts a cross-sectional rear view of the handle assembly of FIG. 7A, where the rotatable housing of FIG. 12 is rotated to the second rotational position relative to the proximal cap of FIG. 13, where the second rotational position of the rotatable housing corresponds to the articulation assembly of FIG. 3 in an articulated configuration, taken along line 15-15 of FIG. 11.

Next, the operator may rotate rotatable housing (220) toward the non-articulated configuration to the position shown in FIGS. 14B and 15B. At the position shown in FIGS. 14B and 15B, rotatable housing (220) is rotated closer to the position corresponding to a non-articulated configuration of end effector (180). However, end effector (180) is still partially articulated at the stage depicted in FIGS. 14B and 15B. As rotatable housing (220) moves from the position in FIGS. 14A and 15A to the position in FIGS. 14B and 15B, radially protruding ridge (226) rotates toward camming projection (214) until radially protruding ridge (226) is camming against and positioned under camming projection (214). Therefore, radially protruding ridge (226) is in contact with camming projection (214) such that the resilient nature of cantilever arm (212) and/or camming projections (214) flexes cantilever arm (212) and/or camming projections (214) outwardly from the natural position to the flexed position.

As radially protruding ridge (226) begins to make contact with camming projections (214), the operator may begin to feel resistance caused from the frictional braking force between ridge (226) and projections (214). The resistance felt by the operator may indicate that end effector (180) is almost at the non-articulated configuration. Additionally, as shown in FIG. 15B, body (122) of handle assembly (120) may include an interior cutout (121) that is dimensioned to accommodate flexing of cantilever arm (212) and/or camming projections (214).

Figure 14C:
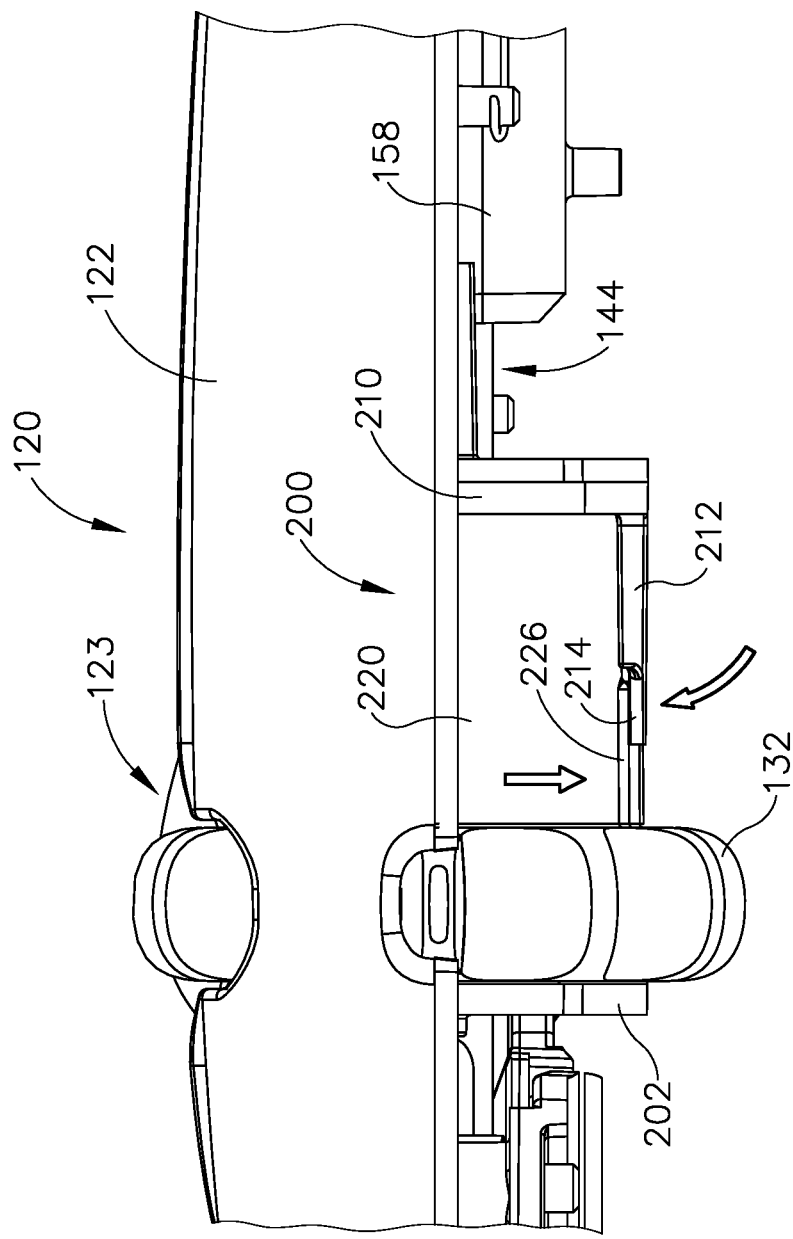
FIG. 14C depicts a top plan view of the handle assembly of FIG. 7A, with a portion of the handle assembly omitted, where the rotatable housing of FIG. 12 is rotated to a third rotational position relative to the proximal cap of FIG. 13, where the third rotational position of the rotatable housing corresponds to the articulation assembly of FIG. 3 in the non-articulated configuration.
Figure 15C:
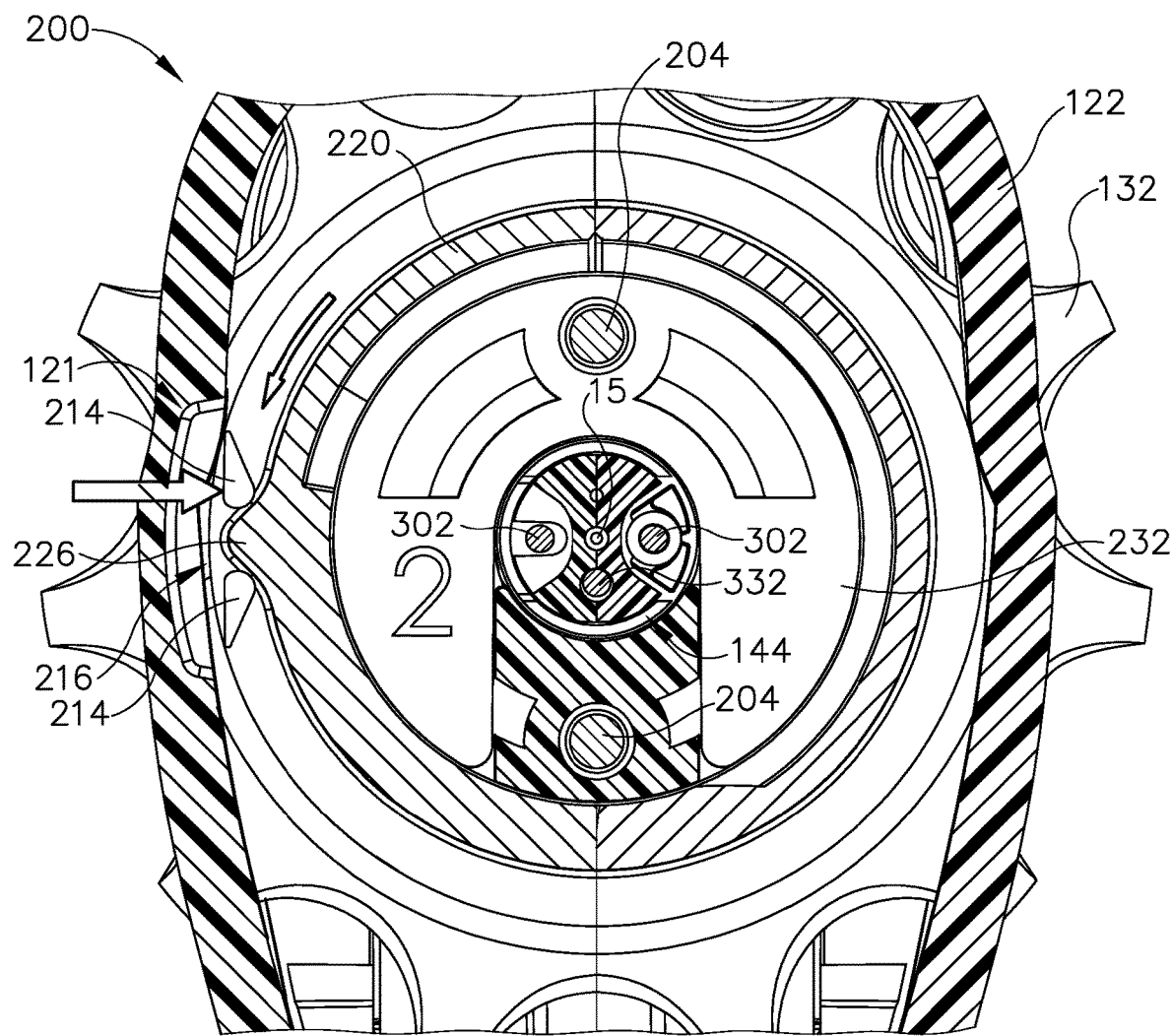
FIG. 15C depicts a cross-sectional rear view of the handle assembly of FIG. 7A, where the rotatable housing of FIG. 12 is rotated to the third rotational position relative to the proximal cap of FIG. 13, where the third rotational position of the rotatable housing corresponds to the articulation assembly of FIG. 3 in the non-articulated configuration, taken along line 15-15 of FIG. 11.

Next, the operator may further rotate rotatable housing (220) from the position shown in FIGS. 14B and 15B to the position shown in FIGS. 14C and 15C. At the position shown in FIGS. 14C and 15C, rotatable housing (220) is rotated to the position corresponding to the non-articulated configuration of end effector (180). As rotatable housing (220) rotates from the position shown in FIGS. 14B and 15B to the position shown in FIGS. 14C and 15C, radially protruding ridge (226) no longer cams against camming projections (214). Thus, radially protruding ridge (226) is housed within open slot (226) defined by camming projections (214). When radially protruding ridge (226) no longer cams against camming projections (214), the resilient nature of cantilever arm (212) and/or camming projections (214) may force cantilever arm (212) and/or camming projections (214) to return to the natural position (as shown in FIGS. 14A, 14C, 15A, 15C). As camming projections (214) and/or cantilever arm (212) return to the natural position, camming projections (214) may contact an exterior of rotatable housing (220) to provide tactile and/or audible feedback to an operator indicating end effector (180) and articulation section (110) have returned to the non-articulated configuration. In other words, camming projections (214) and/or cantilever arm (212) may snap back into the natural position to provide tactile and/or audible feedback to an operator indicting end effector (180) and articulation section (11) have returned to the non-articulated configuration.

Additionally or alternatively, if the operator tried to rotate rotatable housing (220) out of the non-articulated configuration, the operator may encounter sufficient resistance from the frictional braking force between camming projections (214) and radially protruding ridge (226) to indicate to the operator that rotatable housing (220) may be rotating to a position other than the non-articulated configuration. Additionally, the frictional braking force provided between camming projections (214) and protruding ridge (226) while ridge (226) is located within slot (216) may prevent accidental rotation of housing (220) out of the non-articulated configuration, which may help accommodate for removing end effector (180) from a patient and the trocar without inadvertently contacting a portion of the trocar.

While the current example shows the operator rotating rotatable housing (220) from an articulated configuration to the non-articulated configuration, it should be understood that the interaction between camming projections (214) and radially protruding ridge (226) may be used to indicate to an operator when end effector (180) and articulation section (110) have moved away from the non-articulated configuration to the articulated configuration as well. Additionally, while the current example utilizes a radially protruding ridge (226) and a pair of camming projections (214) to provide a detent feature, any other suitable elements may be used to form a detent feature as would be apparent to one having ordinary skill in the art in view of the teachings herein. For example, rotatable housing (220) may include a valley instead of a ridge, while cantilever arm (212) may include a radially inwardly oriented projection and be biased against an exterior of rotatable housing (220) toward valley such that when cantilever arm (212) and valley are aligned, the radially inwardly oriented projection of cantilever arm extends within valley.

In addition to providing an audible and/or tactile feedback feature, and in addition to preventing inadvertent deflection of end effector (180) from the non-articulated configuration, cantilever arm (212) and radially protruding ridge (226) may also promote assembly of articulation drive assembly (200) with associated components via motion in a longitudinal direction. In the current example, the open portion of open slot (216) is distally presented such that ridge (226) may assemble with cantilever arm (212) via longitudinal insertion of ridge (226) within open slot (216). In other words, ridge (226) may be assembled with cantilever arm (212) such that during assembly, cantilever arm (212) does not flex from its natural position. In addition, cantilever arm (212) and radially protruding ridge (226) may cooperate to maintain angular alignment of components of articulation drive assembly (200) as articulation drive assembly (200) is assembled with associated components. Thus, cantilever arm (212) and radially protruding ridge (226) may facilitate assembly of at least a portion of instrument (100).

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a body; (b) a shaft assembly extending distally from the body, wherein the shaft assembly defines a longitudinal axis; (c) an articulation section attached to a distal end of the shaft assembly; (d) an end effector located distally relative to the shaft assembly, wherein the end effector is connected to the articulation section; and (e) an articulation drive assembly, wherein the articulation drive assembly is configured to drive the articulation section to deflect the end effector relative to the longitudinal axis from a non-articulated configuration to an articulated configuration, wherein the articulation drive assembly comprises: (i) a rotatable housing rotatably coupled to the body, (ii) a static member fixed relative to the body, and (iii) an indication feature configured to indicate when the end effector is deflected into the non-articulated configuration, wherein the indication feature comprises: (A) a ridge extending from an exterior surface of the rotatable housing, and (B) a cantilever arm defining a slot configured to house the ridge when the end effector is in the non-articulated configuration.

Example 2

The apparatus of Example 1, wherein the slot defines an open end configured to longitudinally receive the ridge without flexing the cantilever arm.

Example 3

The apparatus of any one or more of Examples 1 through 2, wherein the static member further comprises a cap coupling the rotatable housing with the body, wherein the cantilever arm is attached to the cap.

Example 4

The apparatus of Example 3, wherein the ridge is configured to deflect the cantilever arm when the rotatable housing rotates the ridge into or out of the slot.

Example 5

The apparatus of Example 4, wherein the cantilever arm is configured to provide a tactile response to the ridge rotating into or out of the slot.

Example 6

The apparatus of any one or more of Examples 4 through 5, wherein the cantilever arm is configured to provide an audible response to the ridge rotating into or out of the slot.

Example 7

The apparatus of any one or more of Examples 4 through 6, wherein the cantilever arm is configured to provide a frictional braking force in response to the ridge rotating into or out of the slot.

Example 8

The apparatus of any one or more of Examples 4 through 7, wherein the body defines a cutout configured to house the cantilever arm when deflected by the ridge.

Example 9

The apparatus of any one or more of Examples 1 through 8, wherein the cantilever arm comprises a camming projection extending from the static member, wherein the camming projection and the ridge are configured to interact with each other when the end effector is deflected into the non-articulated configuration.

Example 10

The apparatus of Example 9, wherein the camming projection is resilient such that the ridge is configured to deflect the camming projection relative to the rotatable housing from a natural position to a flexed position.

Example 11

The apparatus of Example 10, wherein the camming projection is configured to provide a tactile response against the rotatable housing when moving from the flexed position to the natural position.

Example 12

The apparatus of any one or more of Examples 9 through 11, wherein the ridge comprises a radial contour.

Example 13

The apparatus of any one or more of Examples 1 through 12, wherein the end effector comprises at least one electrode operable to apply RF electrosurgical energy to tissue.

Example 14

The apparatus of any one or more of Examples 1 through 13, wherein the rotatable housing is configured to house a portion of the shaft assembly.

Example 15

The apparatus of Example 14, wherein the rotatable housing is configured to rotate relative to the shaft assembly.

Example 16

The apparatus of any one or more of Examples 14 through 15, wherein the shaft assembly is configured to translate relative to the rotatable housing.

Example 17

An apparatus comprising: (a) a body; (b) a shaft assembly extending distally from the body, wherein the shaft assembly defines a longitudinal axis; (c) an articulation section attached to a distal end of the shaft assembly; (d) an end effector located distally relative to the shaft assembly, wherein the end effector is connected to the articulation section; and (e) an articulation drive assembly, wherein the articulation drive assembly is configured to drive the articulation section to thereby deflect the end effector relative to the longitudinal axis from a non-articulated configuration to an articulated configuration, wherein the articulation drive assembly comprises: (i) a housing rotatably coupled with the body, wherein the housing further comprises a radially extending ridge, (ii) a cap coupled with the housing, wherein the cap is fixed to the body, and (iii) a resilient indication feature extending from the cap toward the ridge, wherein the ridge is configured to flex the resilient indication feature to snap against the housing in response to the end effector deflecting into the non-articulated configuration.

Example 18

The apparatus of Example 17, wherein the resilient indication feature comprises a slot configured to house the ridge when the end effector is in the non-articulated configuration.

Example 19

The apparatus of Example 18, wherein the resilient indication feature is configured to provide a frictional braking force against the housing when the ridge is housed within the slot.

Example 20

An apparatus comprising: (a) a body; (b) a shaft assembly extending distally from the body, wherein the shaft assembly defines a longitudinal axis; (c) an articulation section attached to a distal end of the shaft assembly; (d) an end effector located distally relative to the shaft assembly, wherein the end effector is connected to the articulation section; and (e) an articulation drive assembly, wherein the articulation drive assembly is configured to drive the articulation section to thereby deflect the end effector relative to the longitudinal axis from a non-articulated configuration to an articulated configuration, wherein the articulation drive assembly comprises: (i) a cap fixed to the body, and (ii) a rotatable housing rotatably coupled to the cap, wherein the rotatable housing comprises a ridge, wherein the cap comprises a resilient indication feature configured to interact with the ridge to provide a tactile response in response to the end effector deflecting into the non-articulated configuration.

IV. Miscellaneous

It should be understood that any of the versions of the instruments described herein may include various other features in addition to or in lieu of those described above. By way of example only, any of the devices herein may also include one or more of the various features disclosed in any of the various references that are incorporated by reference herein. For instance, the teachings herein may be readily combined with various teachings in U.S. Pat. No. 9,526,565, the disclosure of which is incorporated by reference herein; U.S. Pat. No. 9,492,224, the disclosure of which is incorporated by reference herein; and/or U.S. Pub. No. 2016/0100882, issued as U.S. Pat. No. 10,292,758, the disclosure of which is incorporated by reference herein. Various suitable ways in which such teachings may be combined will be apparent to those of ordinary skill in the art.

It should also be understood that any of the devices described herein may be modified to include a motor or other electrically powered device to drive an otherwise manually moved component. Various examples of such modifications are described in U.S. Pub. No. 2012/0116379, entitled "Motor Driven Electrosurgical Device with Mechanical and Electrical Feedback," published May 10, 2012, issued as U.S. Pat. No. 9,161,803 on Oct. 20, 2015, the disclosure of which is incorporated by reference herein. Various other suitable ways in which a motor or other electrically powered device may be incorporated into any of the devices herein will be apparent to those of ordinary skill in the art in view of the teachings herein.

It should also be understood that any of the devices described herein may be modified to contain most, if not all, of the required components within the medical device itself. More specifically, the devices described herein may be adapted to use an internal or attachable power source instead of requiring the device to be plugged into an external power source by a cable. Various examples of how medical devices may be adapted to include a portable power source are disclosed in U.S. Provisional Application Ser. No. 61/410,603, filed Nov. 5, 2010, entitled "Energy-Based Surgical Instruments," the disclosure of which is incorporated by reference herein. Various other suitable ways in which a power source may be incorporated into any of the devices herein will be apparent to those of ordinary skill in the art in view of the teachings herein.

While the examples herein are described mainly in the context of electrosurgical instruments, it should be understood that various teachings herein may be readily applied to a variety of other types of devices. By way of example only, the various teachings herein may be readily applied to other types of electrosurgical instruments, tissue graspers, tissue retrieval pouch deploying instruments, surgical staplers, surgical clip appliers, ultrasonic surgical instruments, etc. It should also be understood that the teachings herein may be readily applied to any of the instruments described in any of the references cited herein, such that the teachings herein may be readily combined with the teachings of any of the references cited herein in numerous ways. Other types of instruments into which the teachings herein may be incorporated will be apparent to those of ordinary skill in the art.

In versions where the teachings herein are applied to a surgical stapling instrument, it should be understood that the teachings herein may be combined with the teachings of one or more of the following, the disclosures of all of which are incorporated by reference herein: U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pub. No. 2010/0264193, entitled "Surgical Stapling Instrument with An Articulatable End Effector," published Oct. 21, 2010, issued as U.S. Pat. No. 8,408,439 on Apr. 2, 2013; and U.S. Pub. No. 2012/0239012, entitled "Motor-Driven Surgical Cutting Instrument with Electric Actuator Directional Control Assembly," published Sep. 20, 2012, issued as U.S. Pat. No. 8,453,914 on Jun. 4, 2013. Other suitable ways in which the teachings herein may be applied to a surgical stapling instrument will be apparent to those of ordinary skill in the art in view of the teachings herein.

In versions where the teachings herein are applied to an ultrasonic surgical instrument, it should be understood that some such instruments may lack a translating firing beam. The components described herein for translating a firing beam may instead simply translate a jaw closing member. Alternatively, such translating features may simply be omitted. In any case, it should be understood that the teachings herein may be combined with the teachings of one or more of the following: U.S. Pat. Pub. No. 2006/0079874, entitled "Tissue Pad for Use with an Ultrasonic Surgical Instrument," published Apr. 13, 2006, now abandoned, the disclosure of which is incorporated by reference herein; U.S. Pat. Pub. No. 2007/0191713, entitled "Ultrasonic Device for Cutting and Coagulating," published Aug. 16, 2007, now abandoned, the disclosure of which is incorporated by reference herein; U.S. Pat. Pub. No. 2007/0282333, entitled "Ultrasonic Waveguide and Blade," published Dec. 6, 2007, now abandoned, the disclosure of which is incorporated by reference herein; U.S. Pat. Pub. No. 2008/0200940, entitled "Ultrasonic Device for Cutting and Coagulating," published Aug. 21, 2008, now abandoned, the disclosure of which is incorporated by reference herein; U.S. Pat. Pub. No. 2011/0015660, entitled "Rotating Transducer Mount for Ultrasonic Surgical Instruments," published Jan. 20, 2011, issued as U.S. Pat. No. 8,461,744 on Jun. 11, 2013, the disclosure of which is incorporated by reference herein; U.S. Pat. No. 6,500,176, entitled "Electrosurgical Systems and Techniques for Sealing Tissue," issued Dec. 31, 2002, the disclosure of which is incorporated by reference herein; U.S. Pat. Pub. No. 2011/0087218, entitled "Surgical Instrument Comprising First and Second Drive Systems Actuatable by a Common Trigger Mechanism," published Apr. 14, 2011, issued as U.S. Pat. No. 8,939,974 on Jan. 27, 2015, the disclosure of which is incorporated by reference herein; and/or U.S. Pat. No. 6,783,524, entitled "Robotic Surgical Tool with Ultrasound Cauterizing and Cutting Instrument," issued Aug. 31, 2004, the disclosure of which is incorporated by reference herein. Other suitable ways in which the teachings herein may be applied to an ultrasonic surgical instrument will be apparent to those of ordinary skill in the art in view of the teachings herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, configurationments, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, configurationments, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. An apparatus comprising:
(a) a shaft assembly defining a longitudinal axis;
(b) an articulation section;

(c) an end effector, wherein the articulation section is interposed between the shaft assembly and the end effector; and (d) an articulation drive assembly, wherein the articulation drive assembly is configured to drive the articulation section to deflect the end effector relative to the longitudinal axis from a non-articulated configuration to an articulated configuration, wherein the articulation drive assembly comprises:
  (i) a rotatable member rotatable relative to the shaft assembly,
  (ii) a static cap, wherein the rotatable member is configured to rotate relative to the static cap, wherein the static cap defines an opening, wherein the shaft assembly extends through the opening of the static cap such that a proximal portion of the shaft assembly extends proximally from the static cap and a distal portion of the shaft assembly extends distally from the static cap, and
  (iii) an indication feature configured to indicate when the end effector is positioned in the non-articulated configuration, wherein the indication feature comprises:
    (A) a ridge extending from an exterior surface of the rotatable member, and
    (B) a cantilever arm directly fixed to the static cap.

2. The apparatus of claim 1, wherein the opening of the static cap comprises a through hole.

3. The apparatus of claim 1, wherein the rotatable member comprises a rotatable housing.

4. The apparatus of claim 3, wherein the rotatable housing comprises a first internal threading.

5. The apparatus of claim 4, wherein the articulation drive assembly further comprises a first lead screw comprising a first external threading, wherein the first internal threading of the rotatable housing is operatively engaged with the first external threading of the first lead screw.

6. The apparatus of claim 5, wherein the rotatable housing comprises a second internal threading.

7. The apparatus of claim 6, wherein the articulation drive assembly further comprises a second lead screw comprising a second external threading, wherein the second internal threading of the rotatable housing is operatively engaged with the second external threading of the second lead screw.

8. The apparatus of claim 7, wherein the rotatable housing is configured to rotate relative to the shaft assembly in a first rotational direction to thereby drive translation of the first lead screw and the second lead screw away from each other.

9. The apparatus of claim 8, wherein the rotatable housing is configured to rotate relative to the shaft assembly in a second rotational direction to thereby drive translation of the first lead screw and the second lead screw toward each other.

10. The apparatus of claim 1, wherein the apparatus further comprises a body, wherein the shaft assembly is interposed between the body and the articulation section.

11. The apparatus of claim 10, wherein the body comprises a handle assembly.

12. The apparatus of claim 1, wherein the cantilever arm defines a slot dimensioned to house the ridge while the end effector is in the non-articulated configuration.

13. The apparatus of claim 1, wherein the cantilever arm is resilient such that the cantilever arm is configured to flex as the end effector is deflected into and out of the non-articulated configuration.

14. The apparatus of claim 13, wherein the cantilever arm further comprises a pair of camming projections.

15. The apparatus of claim 1, wherein the end effector comprises a first jaw and a second jaw configured to pivot relative to each other.

16. An apparatus comprising:
(a) a shaft assembly defining a longitudinal axis;
(b) an articulation section;
(c) an end effector, wherein the articulation section is interposed between the shaft assembly and the end effector; and
(d) an articulation drive assembly, wherein the articulation drive assembly is configured to drive the articulation section to deflect the end effector relative to the longitudinal axis from a non-articulated configuration to an articulated configuration, wherein the articulation drive assembly comprises:
  (i) a rotatable member rotatable relative to the shaft assembly,
  (ii) a static cap, wherein the rotatable member is configured to rotate relative to the static cap, wherein the static cap defines an opening, wherein the shaft assembly extends through the opening of the static cap such that a proximal portion of the shaft assembly extends proximally from the static cap and a distal portion of the shaft assembly extends distally from the static cap, and
  (iii) a resistance feature configured to inhibit deflection of the end effector out of the non-articulated configuration, wherein the resistance feature comprises:
    (A) a ridge extending from an exterior surface of the rotatable housing, and
    (B) a cantilever arm directly fixed to the static cap.

17. The apparatus of claim 16, wherein the end effector comprises an electrode configured to deliver radiofrequency (RF) energy to tissue.

18. The apparatus of claim 16, wherein the static cap is located proximally relative to the rotatable member.

19. The apparatus of claim 16, wherein the end effector comprises a knife configured to sever tissue.

20. An apparatus comprising:
(a) a shaft assembly defining a longitudinal axis;
(b) an articulation section;
(c) an end effector, wherein the articulation section is interposed between the shaft assembly and the end effector; and
(d) an articulation drive assembly, wherein the articulation drive assembly is configured to drive the articulation section to deflect the end effector relative to the longitudinal axis from a non-articulated configuration to an articulated configuration, wherein the articulation drive assembly comprises:
  (i) a rotatable member rotatable relative to the shaft assembly,
  (ii) a static cap located proximally relative to the rotatable member, wherein the rotatable member is configured to rotate relative to the static cap, and
  (iii) a resistance feature configured to inhibit deflection of the end effector out of the non-articulated configuration, wherein the resistance feature comprises:
    (A) a ridge extending from an exterior surface of the rotatable housing, and
    (B) a cantilever arm directly fixed to the static cap and extending distally from the static cap such that a portion of the cantilever arm is adjacent to the ridge.

* * * * *